(12) United States Patent
Maor et al.

(10) Patent No.: US 8,726,394 B2
(45) Date of Patent: May 13, 2014

(54) METHOD AND SYSTEM OF RUNTIME ANALYSIS

(75) Inventors: Ofer Maor, Tel-Aviv (IL); Eran Tamir, Motza Elite (IL); Tamir Shavro, Herzlia (IL); Mor Griv, Ramat-HaSharon (IL)

(73) Assignee: Seeker Security Ltd., Herzlia Pituach (IL)

( * ) Notice: Subject to any disclaimer, the term of this patent is extended or adjusted under 35 U.S.C. 154(b) by 0 days.

(21) Appl. No.: 13/515,538

(22) PCT Filed: Dec. 14, 2010

(86) PCT No.: PCT/IL2010/001059
§ 371 (c)(1),
(2), (4) Date: Jun. 13, 2012

(87) PCT Pub. No.: WO2011/073982
PCT Pub. Date: Jun. 23, 2011

(65) Prior Publication Data
US 2012/0260344 A1    Oct. 11, 2012

Related U.S. Application Data

(60) Provisional application No. 61/352,412, filed on Jun. 8, 2010, provisional application No. 61/286,401, filed on Dec. 15, 2009.

(51) Int. Cl.
*G06F 21/00* (2013.01)
(52) U.S. Cl.
USPC ............................................ 726/25; 717/124
(58) Field of Classification Search
USPC .................................................... 726/25
See application file for complete search history.

(56) References Cited

U.S. PATENT DOCUMENTS

| 7,072,800 | B1 | 7/2006 | Fernandez et al. |
| 2004/0015762 | A1 | 1/2004 | Klotz et al. |
| 2005/0055325 | A1 | 3/2005 | Dutt et al. |
| 2007/0192863 | A1 | 8/2007 | Kapoor et al. |
| 2007/0214503 | A1 | 9/2007 | Shulman et al. |
| 2008/0120305 | A1 | 5/2008 | Sima et al. |
| 2008/0209567 | A1 | 8/2008 | Lockhart et al. |
| 2008/0295178 | A1* | 11/2008 | Beresniewicz ................. 726/25 |
| 2009/0089869 | A1* | 4/2009 | Varghese ......................... 726/7 |
| 2012/0255023 | A1 | 10/2012 | Maor et al. |

OTHER PUBLICATIONS

International Search Report and the Written Opinion Dated Apr. 13, 2011 From the International Searching Authority Re. Application No. PCT/IL2010/01059.

(Continued)

*Primary Examiner* — Gilberto Barron, Jr.
*Assistant Examiner* — Devin Almeida

(57) ABSTRACT

A method and a system for detecting one or more security vulnerabilities. The method comprises providing test instructions for an application, such as a web application or a client server application, adding test code to a code segment of the application according to the test instructions, sending at least one message to the application according to the test instructions at runtime thereof, monitoring test information pertaining to at least one reaction of the application to the at least one message during an execution of the test code, performing an analysis of the at least one reaction, and detecting a presence or an absence of at least one security vulnerability according to the analysis.

36 Claims, 17 Drawing Sheets

(56) References Cited

OTHER PUBLICATIONS

International Search Report and the Written Opinion Dated Mar. 30, 2011 From the International Searching Authority Re. Application No. PCT/IL2010/01060.

Google "Multiple CRLF Injection / HTTP Response Splitting Vulnerabilities in Google AdWords", Google, Debasis Mohanty, 2 P., Dec. 14, 2006.

Huang et al. "A Testing Framework for Web Application Security Assessment", Computer Networks, 48: 739-761, 2005.

International Preliminary Report on Patentability Dated Jun. 28, 2012 From the International Bureau of WIPO Re. Application No. PCT/IL2010/01059.

International Preliminary Report on Patentability Dated Jun. 28, 2012 From the International Bureau of WIPO Re. Application No. PCT/IL2010/01060.

Official Action Dated Mar. 19, 2013 From the US Patent and Trademark Office Re. U.S. Appl. No. 13/515,545.

Official Action Dated Dec. 6, 2013 From the US Patent and Trademark Office Re. U.S. Appl. No. 13/515,545.

* cited by examiner

FIG. 4D

```
.method family hidebysig instance void Page_Load(object sender, class [mscorlib]System.EventArgs e) cil managed
{
    .maxstack 8
    L_0000: ldc.i8 1048577
    L_0009: call void [zzz]XXX.YYY::Trace(long)
    L_000e: nop
    L_000f: ldc.i8 1048580
    L_0018: call void [zzz]XXX.YYY::Trace(long)
    L_001d: ldstr "Hello World!"
    L_0022: ldc.i8 1048620
    L_002b: call void [zzz]XXX.YYY::Trace(long)
    L_0030: call void [mscorlib]System.Console::WriteLine(string)
    L_0035: ldc.i8 1048600
    L_003e: call void [zzz]XXX.YYY::Trace(long)
    L_0043: nop
    L_0044: ldc.i8 1048626
    L_004d: call void [zzz]XXX.YYY::Trace(long)
    L_0052: ret
}
```

*Injected Segments*

FIG. 4E

METHOD AND SYSTEM OF RUNTIME ANALYSIS

RELATED APPLICATIONS

This application is a National Phase of PCT Patent Application No. PCT/IL2010/001059 having International filing date of Dec. 14, 2010, which claims the benefit of priority of U.S. Provisional Patent Application Nos. 61/286,401 filed on Dec. 15, 2009 and 61/352,412 filed on Jun. 8, 2010. The contents of the above applications are all incorporated herein by reference.

FIELD AND BACKGROUND OF THE INVENTION

The present invention, in some embodiments thereof, relates to a method and a system for security assessment of web applications and services and, more particularly, but not exclusively, to a method and a system for runtime security assessment of web applications and services.

Computer security issues are becoming more widespread as an ever-increasing number of diverse computer applications are developed. Problems such as viruses, worms, rootkits, spyware, and theft are plaguing the population of computer users and web services. Additionally, as the Internet connects more people to each other, it also is fueling security problems because confidential information is more easily compromised, see U.S. Patent Application Publication No. 2008/0244261 filed on Mar. 29, 2007.

In their attempt to address Web application security, Scott and Sharp selected three types of security vulnerabilities they believed to be particularly important: form modification, SQL injection, and cross-site scripting (XSS), see D. Scott, R. Sharp, Abstracting application-level Web security, in: The 11th International Conference on the World Wide Web, Honolulu, Hi., May 2002, pp. 396-407 and D. Scott, R. Sharp, Developing secure Web applications, IEEE Internet Computing 6 (6) (2002) 38-45, which are incorporated herein by reference. They also suggested that form modification is often used in conjunction with other forms of attacks, for example, structured query language (SQL) injection. SQL injection and XSS account for the majority of Web application security vulnerabilities, see M. Curphey, D. Endler, W. Hau, S. Taylor, T. Smith, A. Russell, G. McKenna, R. Parke, K. McLaughlin, N. Tranter, A. Klien, D. Groves, I. By-Gad, S. Huseby, M. Eizner, R. McNamara, A guide to building secure Web applications, The Open Web Application Security Project v.1.1.1, September 2002, which is incorporated herein by reference.

Different methods and systems have been developed for detecting and preventing web application security vulnerabilities. For example, U.S. Patent Application Publication No. 2007/0074188, filed on Mar. 29, 2007, describes methods, software tools and systems for analyzing software applications, e.g., Web applications, are described. A software application to be analyzed is transformed into an abstract representation which preserves its information flow properties. The abstract interpretation is evaluated to identify security vulnerabilities using, for example, type qualifiers to associate security levels with variables and/or functions in the application being analyzed and type state checking. Runtime guards are inserted into the application to secure identified security vulnerabilities. Another example is described in U.S. Patent Application Publication No. 2008/0209567, filed on Feb. 15, 2008 that describes security assessment and security vulnerability testing of software applications is performed based at least in part on application metadata in order to determine an appropriate assurance level and associated test plan that includes multiple types of analysis. Steps from each test are combined into a "custom" or "application-specific" workflow, and the results of each test may then be correlated with other results to identify potential security vulnerabilities and/or faults. Another example is described in U.S. Patent Application Publication No. 2008/0295178, filed on May 24, 2007 that describes a web application receives a user input with a SQL injection attack string that references a function. The application generates a corresponding statement based on the user input string, which the application sends to a database server. Upon receiving the statement, the database server executes the statement that invokes the referenced function. When invoked, the referenced function stores a value. The presence of the stored value indicates that the database server invoked the function. Storing the value indicative of the function invocation identifies a security vulnerability of the web application to SQL injection attacks, since the function reference is introduced solely through user input and function invocation is not intended by the application. This provides proof of SQL injection security vulnerability of the application.

SUMMARY OF THE INVENTION

According to some embodiments of the present invention there is provided a method for detecting one or more security vulnerabilities. The method comprises providing test instructions for an application being a web application or a client server application, adding test code which include at least one debug operator and/or instructions which are injected to the program code environment to a code segment of the application according to the test instructions, sending at least one message to the application according to the test instructions at runtime thereof, monitoring test information, such as debugging and/or profiling information pertaining to at least one reaction of the application to the at least one message during an execution of the test code, performing an analysis of the at least one reaction, and detecting a presence or an absence of at least one security vulnerability according to the analysis.

Optionally, the at least one security vulnerability is selected from a group consisting of a structured query language (SQL) injection, a directory traversal, a lightweight directory access protocol (LDAP) Injection, an extensible markup language (XML) path (XPath) injection, operating system (OS) commanding, a simple mail transport protocol (SMTP) injection, carriage return line feed (CRLF) injection, a cross to site scripting (XSS), log file injection, improper logout, username/password enumeration, no session expiration, and detailer error messages.

Optionally, the test information includes data describing an influence of the at least one message on the code execution of the application at the runtime.

Optionally, the method comprises repeating the method with additional test instructions instead of the test instructions.

More optionally, the repeating is performed in each of a plurality of testing sessions; further comprising adding the at least one security vulnerability to a report in each the testing session.

More optionally, the additional test instructions are selected according to the presence or the absence.

More optionally, the repeating is performed in each of a plurality of testing sessions, each the testing session being selected according to a model defining a plurality of connections among the plurality of testing sessions.

More optionally, the model is defined by at least one of a graph and a state machine.

More optionally, each the testing session being selected according an outcome of a previous testing session.

Optionally, the method further comprises establishing a connection to with an application and using the connection for identifying the at least one reaction, the providing being performed according to the identifying.

Optionally, the method comprises providing a model defining a plurality of connections among a plurality of testing session records outlining at least a portion of the test instructions; wherein at least the sending and the monitoring are repetitively performed in a plurality of testing sessions selected according to the model and defined according to a group of the plurality of testing session records.

More optionally, at least one member of the group is selected according to an outcome of at least one of the plurality of testing sessions.

Optionally, the method comprises monitoring behavioral changes of an original code of the application at the runtime period and performing the detecting according to the changes.

Optionally, the sending comprises using a dummy user having a unique address for opening a page having injected data.

Optionally, the detecting comprises detecting a code segment posing the security vulnerability in the code of the application.

Optionally, the method comprises presenting the code segment to a user.

Optionally, the method comprises generating an exploit module to the security vulnerability and providing the exploit module to a user.

Optionally, the method comprises generating a report including the exploit module so as to allow the demonstrating of the security vulnerability.

More optionally, the report includes at least one of a vulnerable page screenshot that allows viewing the final result of the security vulnerability and a set of step-by-step instructions that define how to reproduce the security vulnerability.

More optionally, the generating is performed according to a set of instructions that is based on a behavior of the security vulnerability.

Optionally, the detecting comprises identifying a functionality of a validation/sanitation filter.

More optionally, the identifying is performed by identifying an attack not filtered by the validation/sanitation filter.

Optionally, the providing comprises selecting data application record describing an interface data pertaining to the application from a plurality of data application records and generating the at least one message according to the data application.

Optionally, the monitoring comprises tracking whether a certain string is modified at the runtime.

More optionally, the string is a member of a group consisting of a string provided by the at least one message, at least a portion of a string that function as an input of an executed code of the application, and an output of the application.

Optionally, the monitoring comprises tracking a runtime exception at the runtime, the detecting being performed according to the runtime exception.

Optionally, the application having a plurality of application components in a plurality of network nodes. The adding comprises adding test code to each application component. The monitoring comprises monitoring message traffic between the plurality of application components.

According to some embodiments of the present invention there is provided a system for detecting at least one security vulnerability at runtime. The system comprises a repository storing test instructions, a network interface for sending at least one message to an application according to the test instructions at runtime thereof, the application being a web application or a client server application, a code interface for adding test code to a code segment of the application according to the test instructions and receiving test information pertaining to at least one reaction of the application to the at least one message during an execution of the test code, and a testing unit for detecting at least one security vulnerability according to an analysis of the at least one reaction.

Optionally, the repository stores a plurality of testing session records defining at least a portion of the test instructions, the network interface being configured for sending a plurality of messages in a plurality of testing sessions, each the message being generated according to a different member of a group of the plurality of testing session records.

Optionally, the code interface comprises a code flow tracker that facilitates a code coverage aggregation, the testing unit detects the at least one security vulnerability according to an analysis if the code coverage aggregation.

Optionally, the code interface comprises a code flow tracker that compares code flow outlines of a multi parameter message with different parameter combinations, the testing unit detects the at least one security vulnerability by an analysis of an executed code generated in response to the multi parameter message.

More optionally, the system further comprises a model defining a plurality of connection among the plurality of testing session records, the group being gradually generated at the runtime according to the plurality of connection.

Optionally, the repository stores a plurality of testing session records, further comprising an analyzer configured for managing a testing process by dynamically selecting at least one of the plurality of testing sessions according to the test information, the at least one message being defined according to the at least one testing session.

According to some embodiments of the present invention there is provided a method for detecting one or more security vulnerabilities. The method comprises a) providing a plurality of testing session records each defining a test session for a security vulnerability assessment and a model defining a plurality of connections among the testing session records, b) testing an application according to one of the plurality of testing session records, the application being a web application or a client server application, c) performing an analysis of a reaction of the application to the test session during the execution of the application, d) selecting an additional of the plurality of testing session records according to the model in the light of the analysis, and e) repeating the b) and c) where the testing being held according to the additional testing session.

Optionally, the analysis is of performed according to data aggregated during a previous testing session where the testing is held according to a previous testing session.

According to some embodiments of the present invention there is provided a method for detecting at least one security vulnerability. The method comprises providing test instructions for an application having a plurality of application components in a plurality of network nodes and adding test code, for example at least one debug operator and/or profiling object as described below, to a code segment of each application component according to the test instructions, sending at least one message to the application according to the test instructions at runtime thereof. The method further includes monitoring code flow among the plurality of application components by test information pertaining to at least one reaction of the application to the at least one message during an execution of test code and performing an analysis of the at least one reaction. This allows detecting a presence or an absence of at least one security vulnerability according to said analysis.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4D-4E is an exemplary script depicting the injection and monitoring in a program code execution environment, according to some embodiments of the present invention;

DESCRIPTION OF EMBODIMENTS OF THE INVENTION

Figure 1:
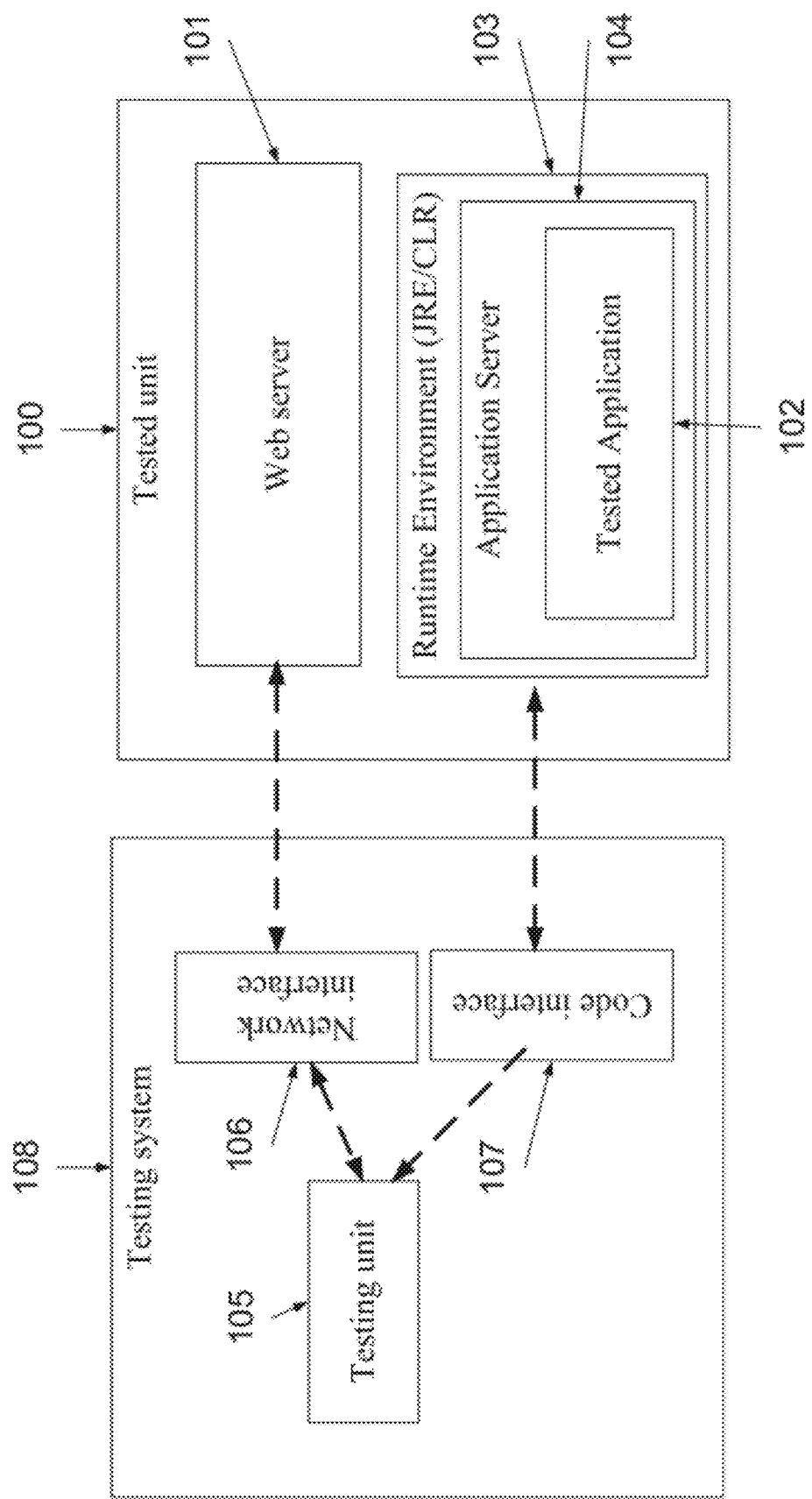
FIG. 1 is a schematic illustration of architecture of a runtime testing system that is connected to an exemplary tested unit, according to some embodiments of the present invention.

The present invention, in some embodiments thereof, relates to a method and a system for security assessment of web applications and services and, more particularly, but not exclusively, to a method and a system for runtime security assessment of web applications and services.

According to some embodiments of the present invention, there is provided a method and a system for detecting one or more security vulnerabilities of a tested application, such as SQL injection and XSS, by monitoring profiling and/or debugging data that is generated at runtime as a reaction to tampered messages. The method includes providing test instructions which are adapted to the web application. The method further includes adding profiling objects and/or one or more debug operators, such as breakpoints and hooks, to a code segment of the web application according to the adapted test instructions. Now, one or more messages, such as HTTP requests, are sent to the web application, optionally via a web server, according to the adapted test instructions. The messages are sent during a runtime period of the tested application. Debugging information pertaining to a reaction, which may be referred to as a response, of the web application to the messages is monitored during an execution of the debug operator. This allows performing an analysis of the reaction and detecting, accordingly the presence or the absence of one or more security vulnerabilities.

Optionally, a plurality of messages is sent in a plurality of consecutive testing sessions. In such a manner, the reactions of the web application to the plurality of messages may be aggregated to allow a comprehensive analysis of the web application behavior. Optionally, the different testing sessions are dynamically selected during the runtime of the web application. As outlined above and described below debugging data which is indicative of the reaction of the web application to received messages is analyzed during the runtime of the web application. In such a manner, new test sessions may be selected during the course of a multi session test. In such a manner, an adaptive multi session test that is changed according to the behavior of the web application may be formed.

Optionally, the testing sessions are held according to a model outlining the connection among a plurality of possible testing sessions, such as a connected graph or a tree graph or a state machine. In such a manner, a different set of messages may be automatically selected for testing different web applications in runtime.

Optionally, the outcome of different testing sessions are recorded and presented to a system operator, optionally in a report. Optionally, an exploit module is generated for each of the detected security vulnerabilities. The exploit module is provided to the operator, allowing her to evaluate the security vulnerabilities by herself.

According to some embodiments of the present invention, there is provided a system for detecting security vulnerabilities in runtime. The system includes a repository for storing test instructions, a network interface for sending messages to a web application according to the test instructions during a runtime period thereof, and a code interface for adding profiling objects and/or debug operators to a code segment of the web application according to the test instructions. The code interface is further designed for receiving debugging information pertaining to the reaction of the web application to the messages during an execution of the profiling objects and/or debug operators. Optionally, the debugging information includes data describing an influence of the messages on the syntax of code execution of the web application at runtime. The code interface and the network interface allow a testing unit to detect one or more security vulnerabilities according to an analysis of the behavior of the web application. Optionally, the testing unit receives the reaction of the web application to the messages. The reaction may be gathered using the profiling objects and/or debug operators, for example as described below. Optionally, the system includes one or more tracker modules of gathering various reactions and reactions of the tested application to the messages.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic illustration of architecture of a runtime testing system 108 that is connected to an exemplary tested unit 100, according to some embodiments of the present invention.

The tested unit 100 executes one or more web applications, web services, and/or databases, for brevity referred to herein as a tested application 102, which are designed to allow remote access via a communication network, such as the Internet or intranet. It should be noted that the runtime testing system 108 may be used for testing web applications which have been developed in various environment, including but not limited to Java, .NET, Transact SQL (T-SQL), and Procedural Language (PL)/SQL. Optionally, the tested unit 100 includes a web server 101, such as Apache, Microsoft™ IIS™, and WebSphere™, and a runtime environment 103, such as Java Virtual Machine (JVM) and Common Language Runtime (CLR), which the standards thereof are incorporated herein by reference. The runtime environment 103 is used by an application server 104, such as Jboss Seam, Weblogic Tomcat, and Websphere. The application server 104 allows executing the tested application 102.

The runtime testing system 108 includes a network interface 106 that that is optionally designed to communicate with the tested application 102 via the web server 101, optionally via a network port. Optionally, the network interface 106 includes a scripting engine, as described below. It should be noted that the network interface 106 may include any type of HTTP client, for example a component generating HTTP requests and allows executing a flow of HTTP requests.

In some embodiments, the tested application is a Client/Server application. For performing the test with a client/server application, the HTTP client should be replaced with a client able to reproduce the client requests, and allow sending modified client requests. Such client requests may be done by means of Web Services/Simple Object Access Protocol (SOAP), Remote Method Invocation (RMI), Distributed Component Object Model (DCOM), and/or any other form of standard or proprietary communication protocol. When performing client/server testing, the tester described below utilizes such a client to emulate the client requests and modifies them with attack vectors. The runtime analyzer analyzes the code execution in an identical manner to the one done in web applications.

This connection allows the runtime testing system 108 to transmit messages to the tested unit 100 and to receive responses therefrom, for example hypertext transfer protocol (HTTP) message and debug response messages and/or information. For brevity, the messages may be referred to herein as messages.

The runtime testing system 108 is designed to execute a number of test sessions, optionally iteratively, for example as described below. In each test session a message is sent to the tested unit 100 and a response of the tested application 108 to the message is intercepted and analyzed, for example as described below.

The runtime testing system 108 includes a testing unit 105 that is optionally connected to a repository for storing a rules, optionally in a dataset that includes a plurality of connected records, each consist a set of instructions for a different test session. As used herein, such a set of instructions may be referred to as a test session record and/or test session node.

The runtime testing system 108 further includes a code interface 107, referred to herein as runtime monitor module 107, that adds debug operators to the code of the tested application and monitors responses to the messages provided by the scripting engine 106 in runtime, during the test sessions, and forwarding the responses for analysis by the testing unit 105. The runtime monitor module 107 receives the responses from the tested application 102 in runtime.

Optionally, the testing unit 105 comprises an analyzer module for analyzing the data monitored by the runtime monitor module 107 during a test process and optionally a response parser for preprocessing the response before it is analyzed. The preprocessing allows correlating the response with testing data that is defined in a respective testing session record. Optionally, the preprocessing may be applied on some or all of the responses.

Figure 2:
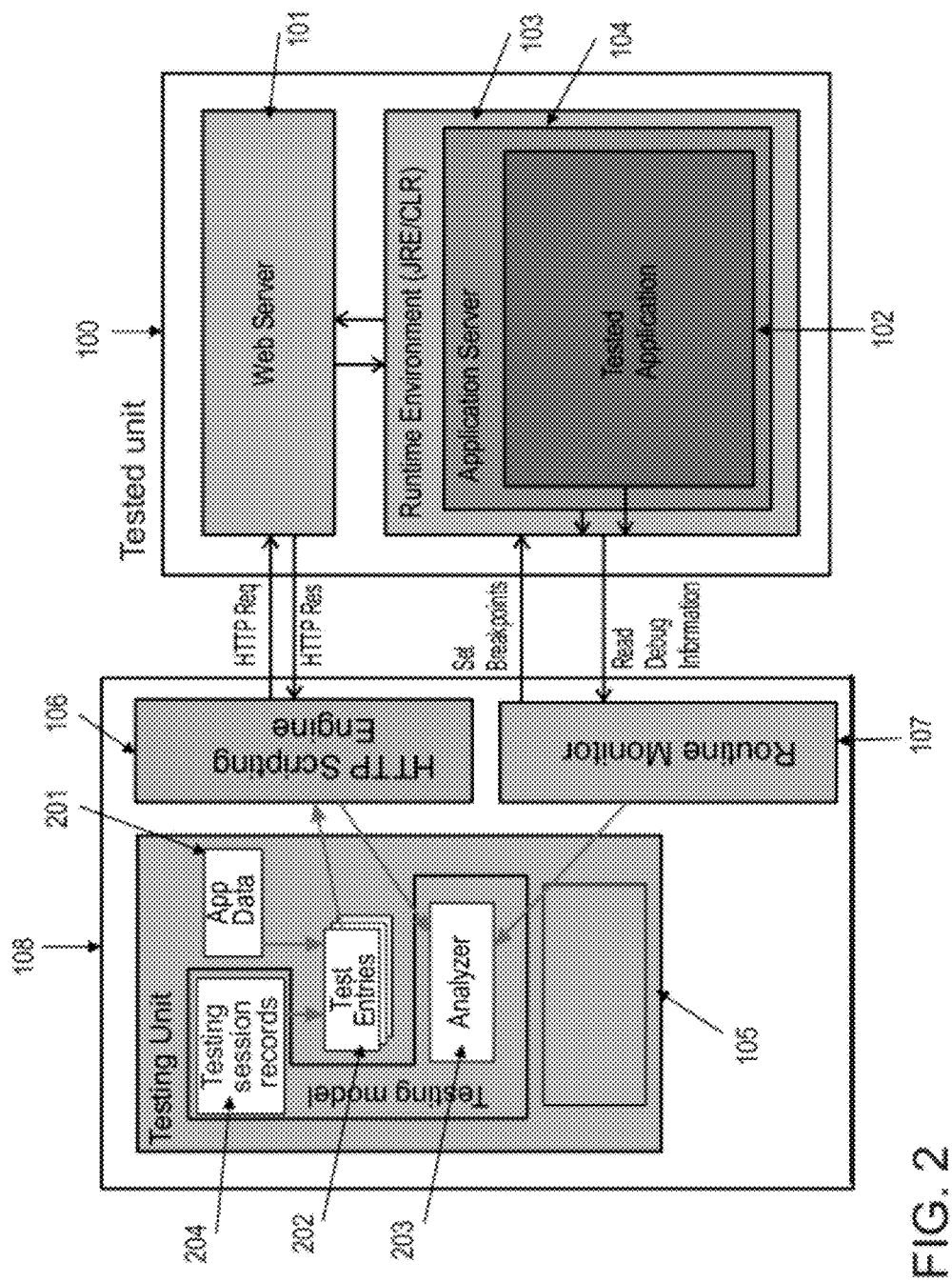
FIG. 2 is a schematic illustration of the runtime testing system and the tested unit of FIG. 1 in which optional components of the runtime testing system are described, according to some embodiments of the present invention.

Reference is now also made to FIG. 2, which is a schematic illustration of the runtime testing system 108 and the tested unit 100 of FIG. 1 in which optional components of the system are described, according to some embodiments of the present invention. As outlined above, the testing unit 105 includes the analyzer module 203 for receiving the responses of the tested application 102 from the runtime monitor module 107. Optionally, the analyzer module 203 further receives the messages which have been inputted during the testing process, and optionally related data such as execution time, from the scripting engine 106. In such a manner, the analyzer module 203 may base its analysis, in runtime, on actual messages and actual responses thereto.

Optionally, the testing unit 105 includes application data records, referred to herein as application data repository 201 or App Data 201. Each application data record includes designated testing instructions, such as application data pertaining to a certain application which may be tested by the runtime testing system 108 for example application data that defines access interface for one or more related application components. In use, a matching application data record may be selected for the tested application 102. For example, the Application data repository 201 of a certain web application includes a collection of HTTP requests that represents valid user traffic, such as uniform resource locators (URLs), parameters, Cookies, Session, Authentication Information, HTTP headers and/or parameter values. For each type of tested application, the Application data repository 201 contains some or all of the information which is required for reproducing some or all of the valid application messages.

As outlined above, the testing unit 105 includes a dataset that includes testing instructions which are optionally divided to a plurality of testing session records each includes set of message instructions 204 which are designed to be combined with a matching application data record from the application data repository 201 that is selected for the tested application to produce test entries, as shown at 202. Optionally, the testing session records are arranged in or associated with a model, such as a graph and a state machine, defining a plurality of connections among a plurality of testing session records, represented as nodes.

The model is used for dynamically determining, according to intermediate results, which testing sessions are used for probing, in runtime, the tested application. Optionally, each testing session record is a node in the graph. In use, an outcome of an analysis of responses received during one testing session outputs of the tested application determine a progress along the graph. The progress defines which additional testing session records, graph nodes, are selected and used for testing the tested application 102. In such an embodiment, a dynamic iterative process in which a test is preformed according to a path of testing session records, which are dynamically built according to the outcome of the previous tests, is held, for example as described below.

Figure 3:
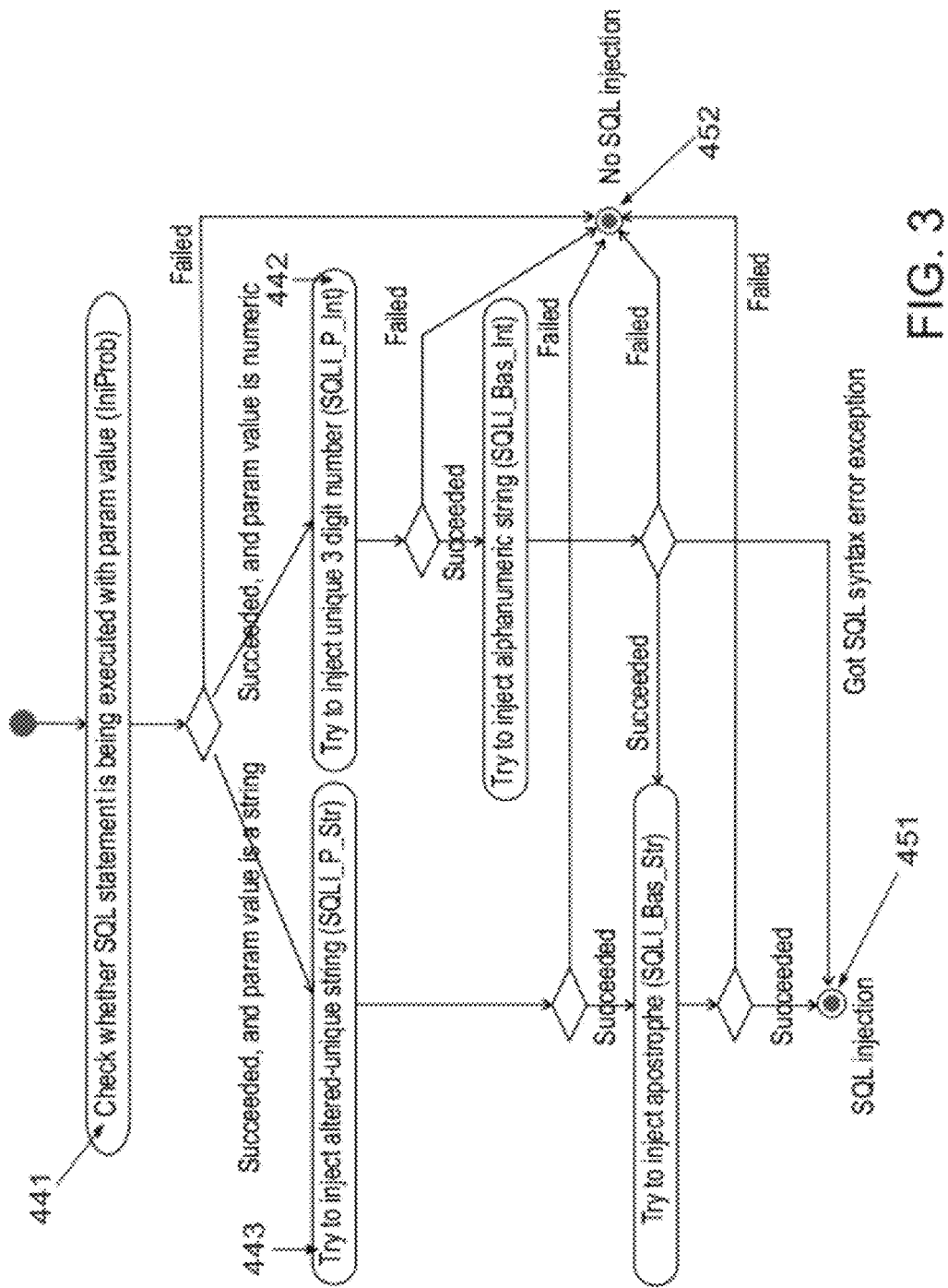
FIG. 3 is a schematic illustration of an exemplary model defining connections between exemplary testing session records, according to some embodiments of the present invention.

For example FIG. 3 depicts is an exemplary model defining connections among exemplary testing sessions which are held according to the outcome of other testing sessions, according to some embodiments of the present invention. In FIG. 3, when a message defined according to an SQL statement with a parameter value, referred to herein as IniProb, succeed, and the parameter value is a string, an altered unique string is injected. However, if the parameter value is a numeric value, a three digit number is injected. As shown at FIG. 3, this process lasts until the graph outlines an ending, as shown at 451 or in 452.

Optionally, the graph includes an initiation node, referred to herein as a prober, that allows generating a message, referred to herein as a normal message, which is not modified with specific testing logic. Such a message may be used to determine which tests are relevant in the context of specific tested code.

Optionally, the graph architecture includes a number of sub graphs, each related to security vulnerability. In such an embodiment, testing sessions may be sequentially performed according to the different sub graphs.

Each testing session record 204 includes test rules such as instructions for modifying the matching application data 201, for example web messages, such as HTTP messages, of the matching application data record from the application data repository 201. The applying of the test rules from a test session record on messages, which are defined in an application data record from the application data repository 201, allows creating one or more testing messages that emulate an attack or otherwise allow detecting a security vulnerability to such an attack. For clarity, as used herein, security vulnerability means any weakness that allows an attacker to reduce a system's information assurance (IA) and/or any weakness that allows an attacker to affect the practice of managing information-related risks.

Additionally, each testing session record may define a code behavior and/or an output behavior that is expected to be expressed in the response to the one or more testing messages which are defined according thereto. In such an embodiment, a testing process is held in a number of testing sessions according to a number of testing session records which are optionally dynamically selected according intermediate results. As outlined above, each one of the testing session records include test rules which are defined and stored for a certain application.

Optionally, some testing sessions define an initial examination in which group of security vulnerabilities is detected, for example whether the code of the tested application is based on SQL statements, and the like.

Figure 4A:
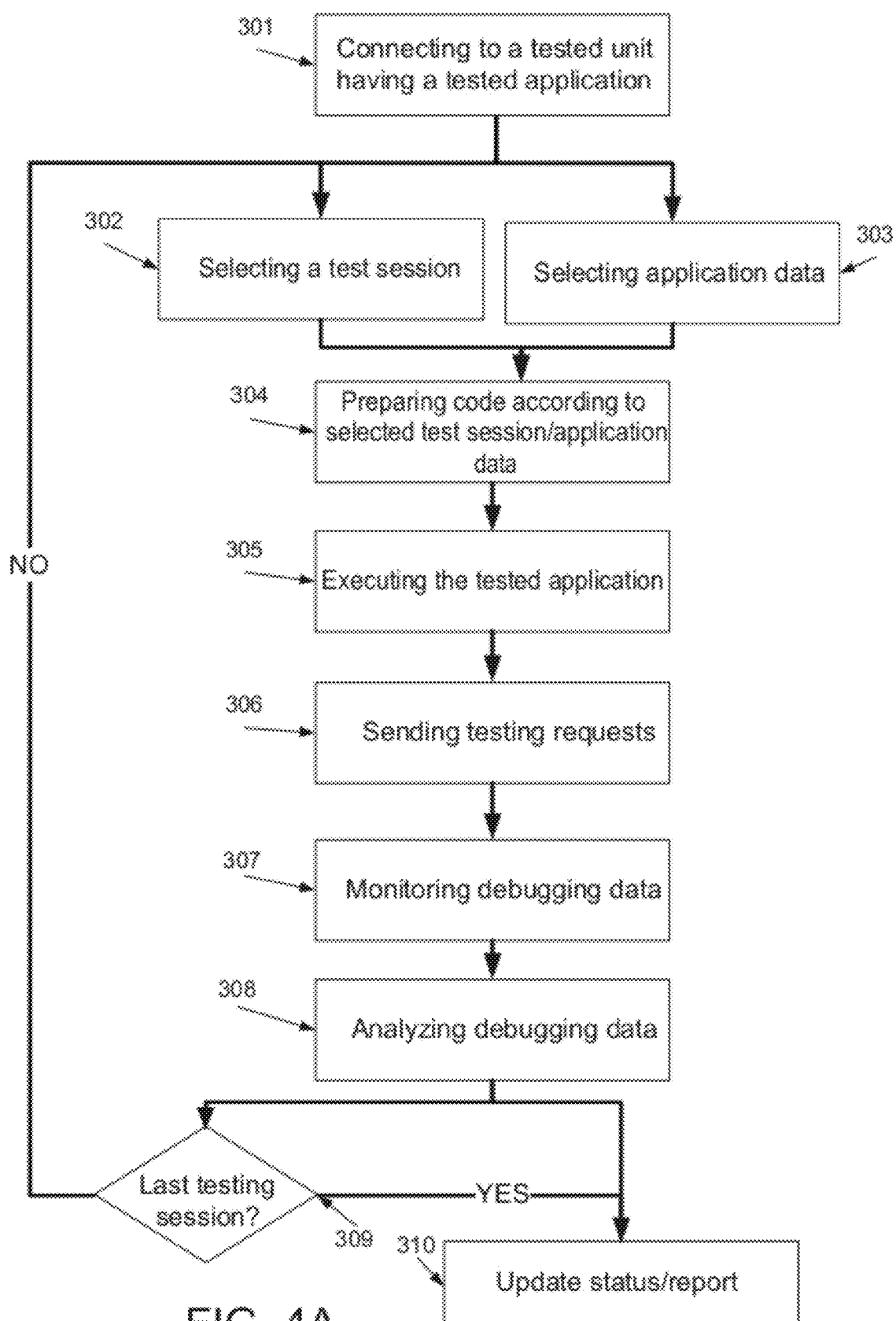
FIG. 4A is a flowchart of a method for testing security vulnerabilities of a web application, according to some embodiments of the present invention.

Reference is now also made to FIG. 4A, which is a flowchart 300 of a method for testing web application security vulnerabilities, according to some embodiments of the present invention. Reference is also made to FIGS. 6A-6E, which are screenshots of a graphical user interface (GUI) for allowing a user to control a testing process, monitor the testing process, and/or receive data from the testing process, according to some embodiments of the present invention.

Figure 6A:
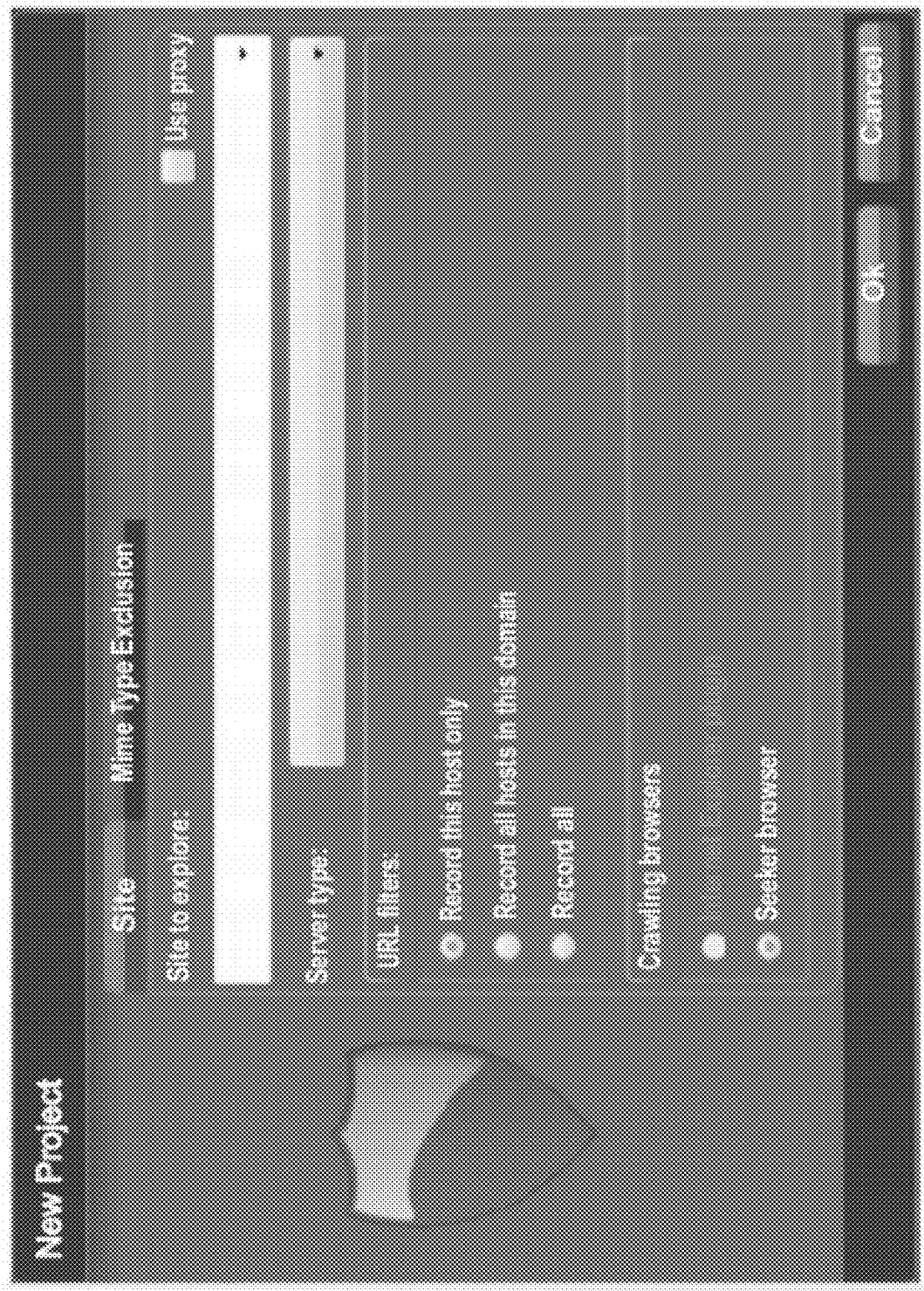
FIGS. 6A-6E are screenshots of a graphical user interface (GUI) for allowing a user to control a testing process, monitor the testing process, and/or receive data from the testing process, according to some embodiments of the present invention.

First, as shown at 301, a connection is established between the runtime testing system 108 and the tested unit 100 that includes the tested application 102. Optionally, as shown at FIG. 6A, a GUI allows the operator to designate a web application by providing the URL thereof.

Now, as shown at 302 and 303, test instructions are selected for the tested unit 100. Optionally, the test instructions are defined in the application data record that is selected from the Application data repository 201 for the tested application 102, for example as described above, and in the testing session record which is selected as described above. As shown at 302, one of the testing session records is selected from the repository 204. Optionally, the selected testing session record associated with a node in a model, such as a graph, defining a plurality of connections among a plurality of testing sessions, for example as described above. As shown at 303, an application data record is selected. Optionally, the selected application data record includes a collection of entries, each describing the interface to invoke an application operation of the tested application 102. Optionally, each interface describes an HTTP message that includes an access process, a URL, parameter names and/or parameter values representing a valid message of the tested application 102.

Now, as shown at 304, the routine monitor 107 prepares the code of the tested application 102 for a testing session, optionally according to instructions in the selected testing session record and/or in the selected data application record. Each testing session record contains instructions for modifying the messages into testing messages, optionally as outlined above and described below. Optionally, the messages defined in the selected application data record are manipulated according to one or more testing rules from the selected testing session record.

The routine monitor 107 sets debug operators, such as debug hooks, breakpoints, watches, and the like, in the code of the tested application according to the testing instructions.

These debug hooks allows identifying suspected code execution events, such as database operation code execution, file system access operations, response writing operations, class loading/unloading operations, memory access operations, string manipulation, session management operations, and the like.

Optionally, the debug operators allow monitoring the activity of the tested unit 100 during a user session, such as a user authentication session, and to determine the validity of the session. This allows the runtime testing system 108 to identify when a certain operation has caused the session to break, thus reestablishing the session, without failing the test process.

Now, as shown at 305, the tested application 102 is executed on the tested unit 100.

Optionally, the execution is initiated by the scripting engine 106 that sends a request via the web server 101 that invokes, in response, the application server 104 and the tested application 102 that resides thereon.

Figure 6B:
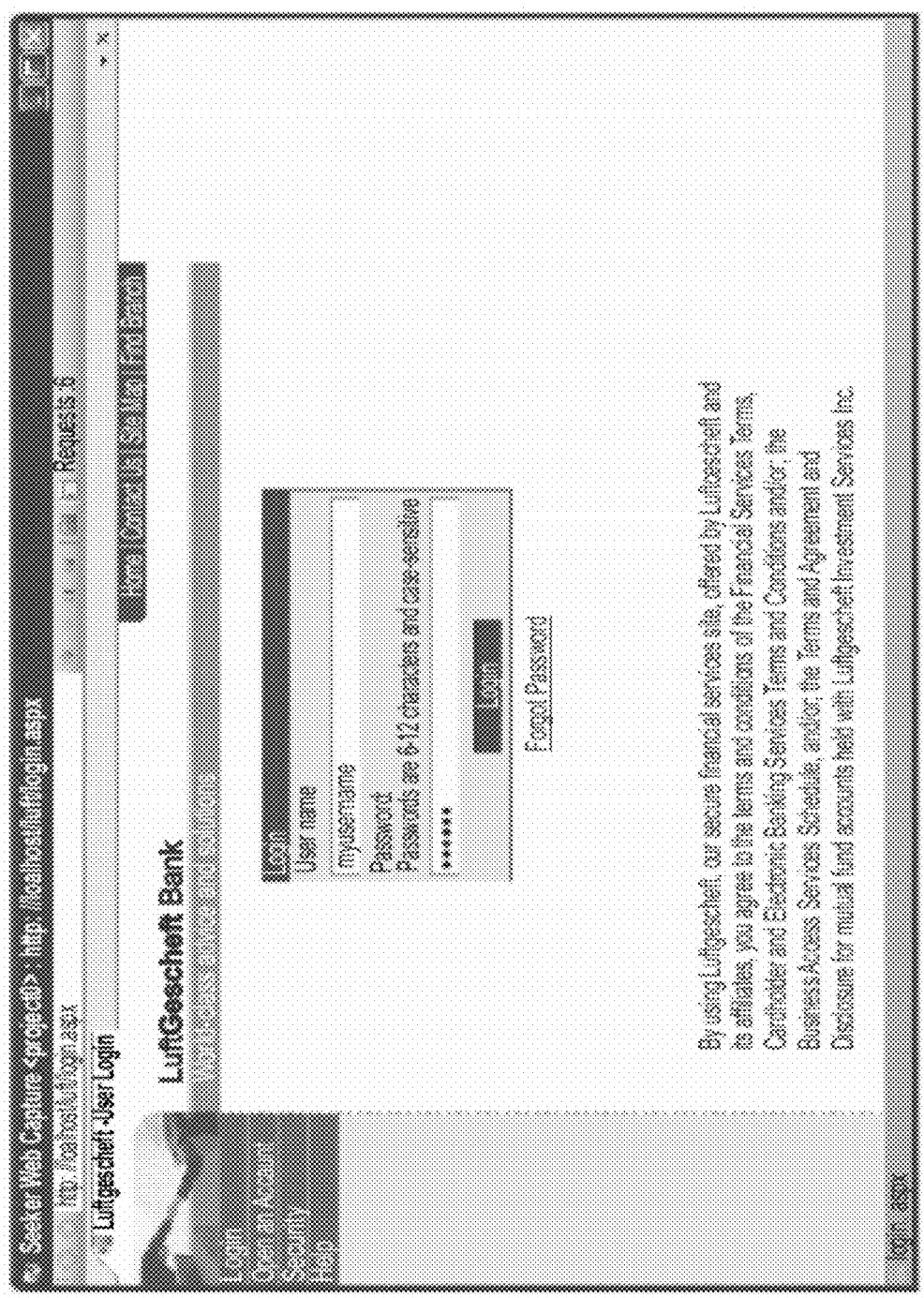

Optionally, this process includes presenting, in runtime, the tested application. For example, FIG. 6B depicts an exemplary GUI presenting a login page through which the testing messages are inputted.

Figure 6C:
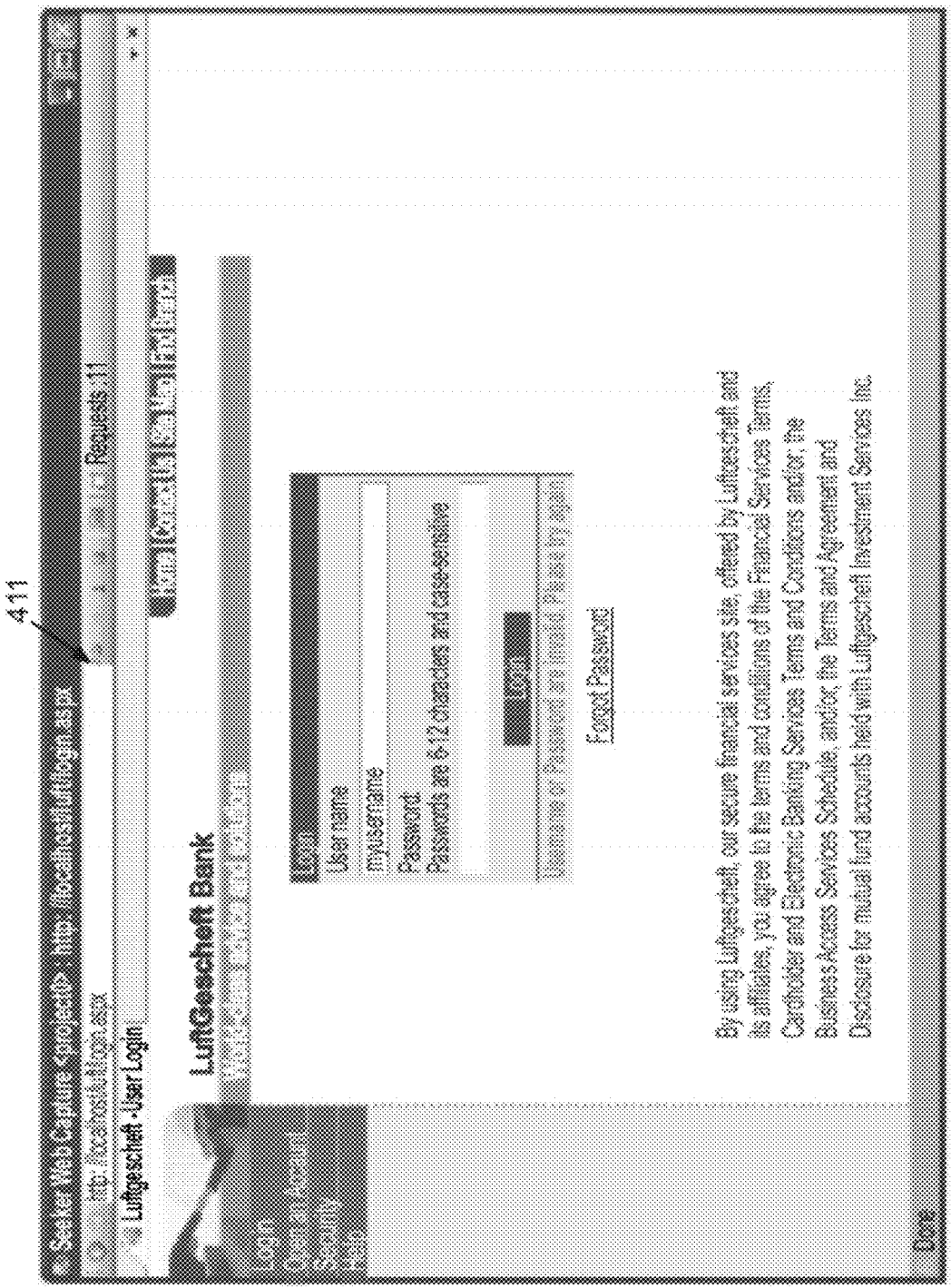

Optionally, the GUI includes a toolbar, or any other component that allows the operator to initiate and/or end the testing process, for example as shown at numeral 11 of FIG. 6C.

Optionally, the presentation allows the operator to determine when to launch the testing process. Optionally, the runtime testing system 108 preprocesses the tested application 102 or a portion thereof, for example a webpage, and display general information about the tested webpage based thereupon. For example, as shown at FIG. 6C the GUI displays general data 422 pertaining to selected webpages 421.

Now, as shown at 306, the scripting engine 106 sends one or more testing messages to the web server 101 while the routine monitor 107 reads, in runtime, debugging information that is generated in response to the testing messages, as shown at 307.

Optionally, as shown at 308, the analyzer 203 analyses the debugging information, optionally according to the selected testing session record and/or the injected testing messages. Optionally, the analyzer 203 performs an analysis by comparing between the debugging information and a set of predicted. The analysis is performed in runtime, after the tested applications have been successfully loaded for execution. Additionally or alternatively, the debugging data is aggregated and optionally stored for an analysis of debugging information that has been accumulated during a number of testing sessions.

According to some embodiments of the present invention, the routine monitor 107 includes one or more tracker modules which are designed to monitor various outputs of the tested application and/or the executed code of the tested application in runtime. Such monitoring is used for detecting various security vulnerabilities. Optionally, the routine monitor 107 includes a string flow tracker and/or a code execution tracker, which are designed to identify when certain tracked strings have gone through certain types of filtering aimed at blocking the execution of a related code segment and/or altering the string. Optionally, the string flow tracker sets various hooks on string manipulation methods and assignment methods according to the adapted test instructions. The string manipulation and assignment methods may result with string modifications, string splitting and/or string duplication that may initiate new string flow tracks. Tracking the hooks activity and output actually traces these modifications to the user input until it reaches execution points.

Identification of this type of validation and/or sanitation may be significant for fine tuning of potential security vulnerability detection. By identifying the exact input validation/sanitation process, the runtime testing system 108 is able to determine whether alternative forms of attacks, which are not blocked and/or filtered by the execution of the related code segment, may prevail and therefore should be considered as potential security vulnerabilities. Furthermore, by identifying the exact input validation/sanitation process false positives may be avoided. The aforementioned identification indicates that certain input validation/sanitation filters are properly implemented by the tested unit 100. In such a manner, the runtime testing system 108 does not classify code segments that cannot be exploited as potential security vulnerabilities as potential security vulnerabilities.

Additionally or alternatively, the routine monitor 107 includes an input flow tracker that is configured for monitoring user inputs which are received during the runtime of the tested applications. Optionally, the input flow tracker identifies when a string, or a substring, provided by a user, optionally via a network port, or as a reaction to a user input, is used and/or manipulated by a specific process, such as a function. For example, the usage may be embedding the string and/or substrings into other strings, modifying the string and/or substrings and the like. In such a manner, the Input-Flow-Tracker may be used for tracking the behavior of the tested application 102 in response to an input.

Additionally or alternatively, the routine monitor 107 includes an output flow tracker for tracking outputs of the tested application 102 in certain execution points.

Additionally or alternatively, the routine monitor 107 includes a code flow tracker that determines, optionally for each message, the outline of the executed code. Optionally, the code flow tracker facilitates a code coverage aggregation that improves the aggregation of the application data during the application data gathering. Normally, a designated test has to be conducted for testing the actual code which is executed in response to a multi parameter message. Thus, when an N designated tests has to be conducted for testing the actual code that is executed in response to a multi parameter message with N potential combinations of parameters. The code flow tracker allows comparing code flow outlines of a multi parameter message with different parameter combinations so as to determine whether the executed code is identical or not. In such a manner, an additional test may be launched only if the code flows are different.

Additionally or alternatively, the code flow tracker facilitates code coverage detection by correlating the actual executed code with a statically analyzed code. In such a manner, if the difference between the actual executed code and the statically analyzed code is above a certain percentage, the code coverage detection defines which percentage of the code in the application is covered by the test process. This can be used to guarantee sufficient coverage or provide information to the user to solve insufficient coverage problems.

Optionally, the information is used for automatically solving insufficient coverage problems. In such an embodiment, the executed code is analyzed and compared with a statistical analysis of the code. If the detected coverage is not complete, branching points where statement determine which code segments are to be executed are detected and used to identify branching conditions. Optionally, a relevant request with relevant parameter information is created to allow reaching additional areas of the code.

Optionally, the routine monitor 107 includes a runtime exception tracker that tracks runtime exceptions. In such a manner, the routine monitor 107 may identify when certain operation has caused an exception. In such a manner, the handling of the runtime to exceptions by the web application may be evaluated so as to determine whether certain attack simulation have been successful or not.

Optionally, the detected web application security vulnerabilities are marked and/or stored for allowing the operator of the tested application 102 to fix these security vulnerabilities. Optionally, pseudo code segments which pose these security vulnerabilities are pinpointed. Optionally, a report presenting or otherwise indicating these code segments is provided to the users so as to allow handling each one of the security vulnerabilities.

Figure 6D:
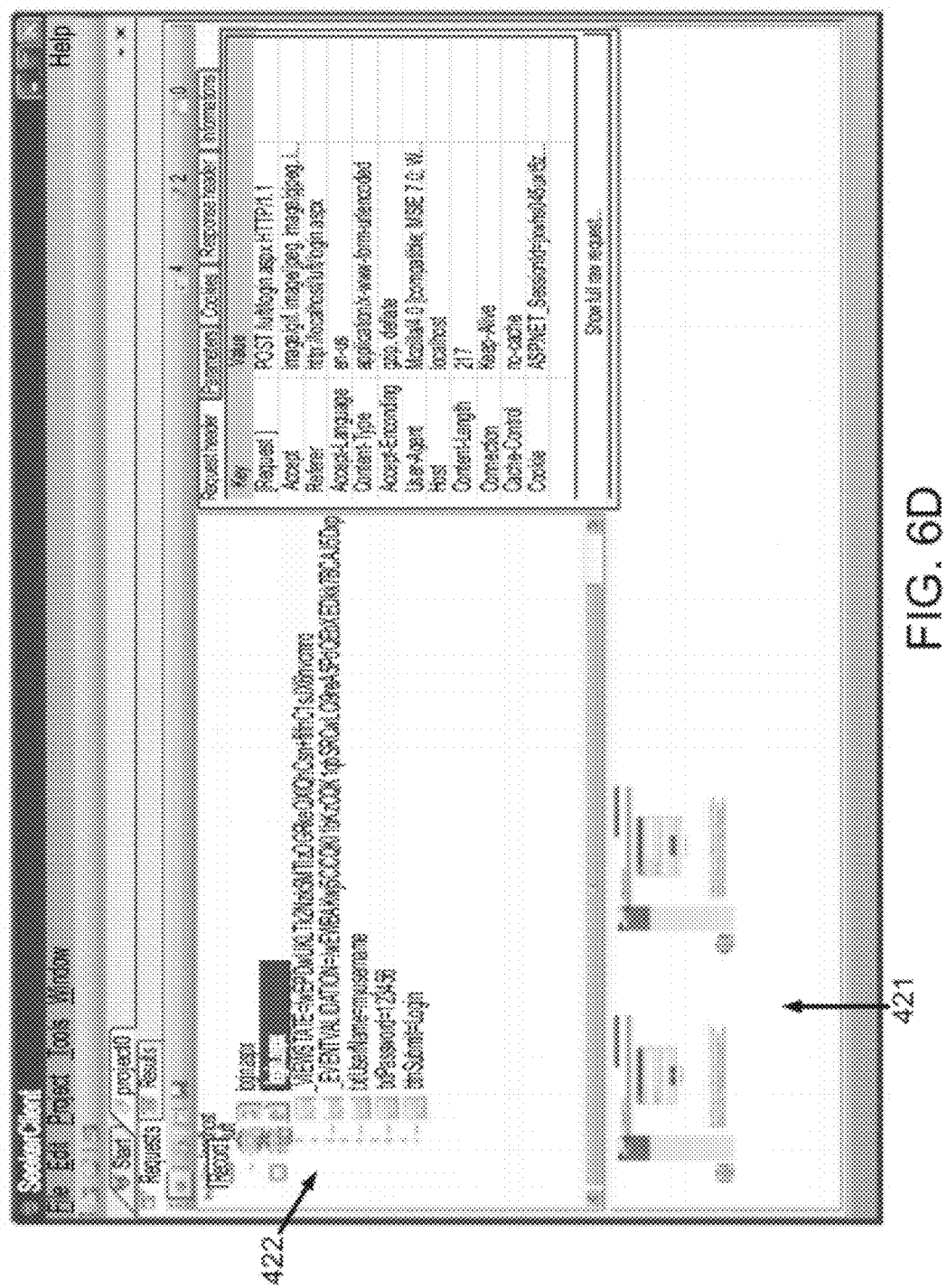
Figure 6E:
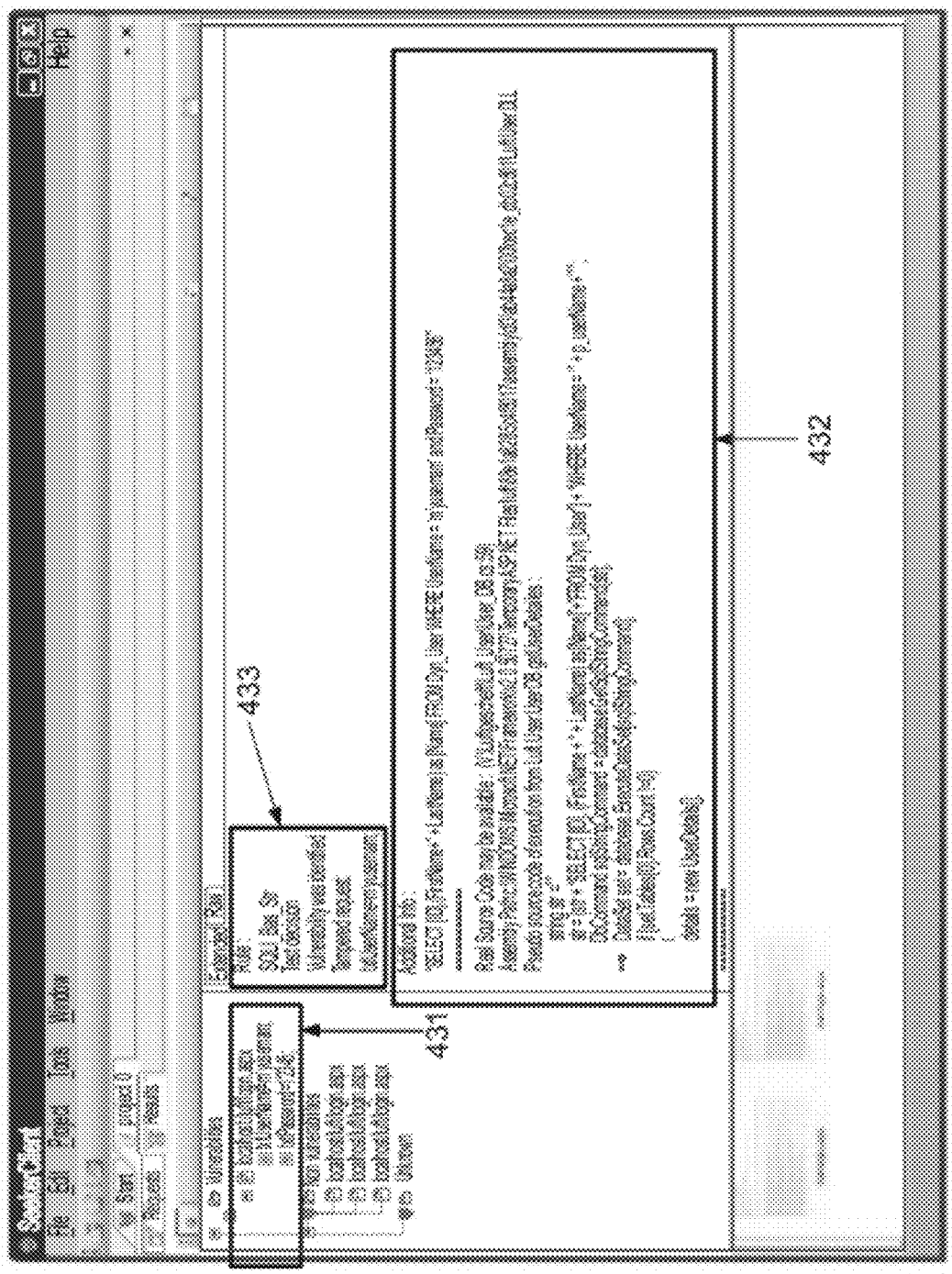

Optionally, the security vulnerabilities are presented to the user, optionally during the runtime of the application, for example using the aforementioned GUI. For instance, FIG. 6D is an image of a GUI that depicts an exemplary webpage that has been monitored in run time and related debugging data which has been analyzed. In FIG. 6D, the GUI presents the parameters of the message, for example txtUserName and txtPassword, as shown at 431 and additional data pertaining to the runtime analysis, for example pseudo codes segment vulnerability 432 and a security vulnerability of related information, such as status 433.

Optionally, some or all the test sessions are used for detecting a security vulnerability that involves more than one webpage, for example a stored/persistent cross site scripting (XSS). For example, one webpage is a simple form that allows inputting a message and another webpage includes a list of messages that every user may see.

In order to detect such security vulnerability, the testing session includes instructions to perform an actual test in steps, where user inputs to a database and responses thereto are followed. Optionally, data transferred between the web pages and the database is tracked and a correlation between pages that receives input from the user and pages that show the data to the user is found. In case it finds a correlation, it analyzes it in order to check if a manipulated input may be used in the detected pages. In general, when such correlation transfers tampered input to and from the database, security vulnerability is detected.

Now, as shown at 309, the testing process is either ended, for example when a testing session record is associated with a node in a graph that does not have child nodes, or repeated with a new testing session record that is selected according to the output of the analysis of the previous testing session. As described above, the new testing session record is selected according to the model. The new selected testing session record is used, together with the selected application data, for conducting another test session of the tested application 102, for example as indicated by numeral 309. This process is iteratively repeated according to the nodes in the connected graph, according to a threshold and/or according to the outcome of one or more of the testing sessions.

As shown at 310, the status of the tested application 102 is updated according to the analysis. For example, if the analysis indicates on one or more web application security vulnerabilities, the status of the tested application 102 is update to reflect its security vulnerability.

Figure 4B:
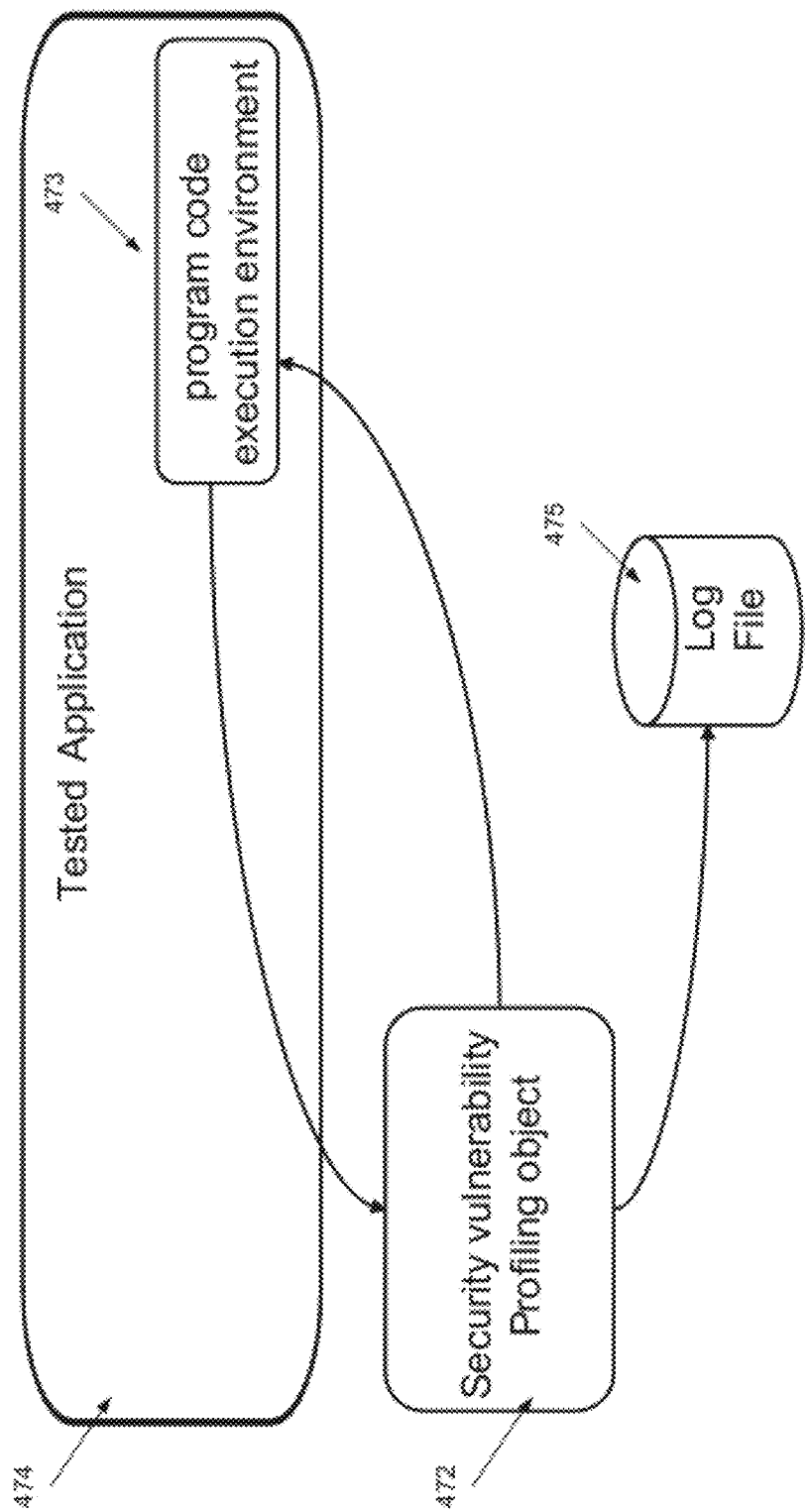
FIG. 4B is a schematic illustration of a security vulnerability profiling object include instructions which are injected to a program code execution environment, according to some embodiments of the present invention.
Figure 4C:
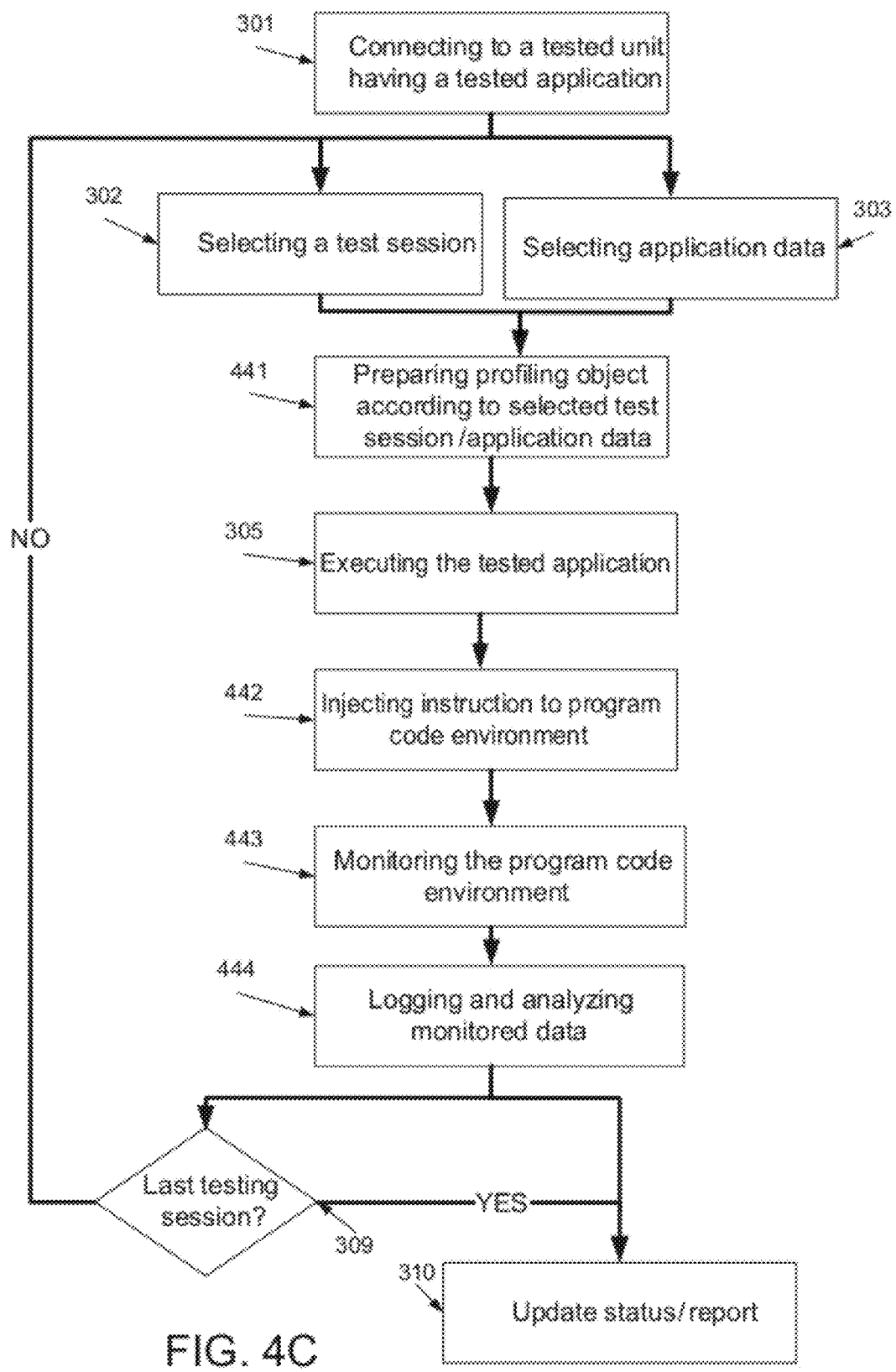
FIG. 4C is a flowchart of a another method for testing security vulnerabilities of a web application, according to some embodiments of the present invention.

According to some embodiments of the present invention, the routine monitor 107 may include a profiling module designed to generate code instructions, referred to herein as a security vulnerability object, which are injected to a program code environment which hosts and executes program code, such as common language runtime (CLR) code of the tested application, and to log security related data generated in response to the injected instructions, pertaining to the tested application. In such a manner, the routine monitor 107 may test web application security vulnerabilities of the tested application without modifying the executed tested applications, for example its binaries and scripts. For example, FIG. 4B is a schematic illustration of a security vulnerability profiling object 472 that includes instructions which are injected to a program code environment 473 that hosts and executes CLR code of a tested application 474 and a log 475 generated and updated by the security vulnerability profiling object 472. Reference is also made to FIG. 4C, which is a flowchart of a method for testing security vulnerabilities in tested applications by injecting instructions to the program code environment, according to some embodiments of the present invention.

Blocks 301-303, 305, and 309-310 are as described above. After 303 and 302, the profiling module of the routine monitor 107 prepares or selects the instructions for injection during a testing session, optionally according to instructions in the selected testing session record and/or in the selected data application record. Optionally, the instructions are defined as CLR code instructions. Now, as shown at 442, while the tested application is executed, as shown at 305, instructions are injected to the program code environment 473, for example using a .Net profiling mechanism. The instructions change the tested process source code in memory where the tested process handles web requests, for example as an internet information server (IIS). The changing of the source code in memory means that file(s) belong to the tested application are not altered and/or accessed. The program code environment is monitored, as shown at 443, facilitating the logging, as shown at 444, of security related data regarding the tested application. Optionally, the instructions contain specially made code sections that allow the routine monitor 107, for example the security vulnerability profiling object 472, to collect data that is used to evaluate and/or identify security vulnerabilities. The logging is optionally done using a profiler without changing the source code. This allows acquiring test information from monitored events and using them with other data pertaining to the tested application, for example data defined in the test entries 202.

In an exemplary scenario, the routine monitor 107 (i.e. profiling object) injects new code instructions which calls back to the routine monitor 107 with data that relates to a specific position of the new code instructions. For example, the injected code sends a current execute line of code and additional information about the method, and the optionally the respective dynamic link library (DLL), to the routine monitor 107 for analysis, allowing the routine monitor 107 to evaluate security vulnerabilities based on this analysis. The routine monitor 107 may create a stack trace of the target application code and identify anomalies in execution per input manipulation. A example of an injection, in C# is as follows:

```
protected void Page_Load(object sender, EventArgs e)
{
Console.WriteLine("Hello World!");
}
``` which translates into the following common intermediate language, Microsoft Intermediate Language (MSIL):

```
.method family hidebysig instance void Page_Load(object sender, class [mscorlib]System.EventArgs e) cil managed
{
.maxstack 8
L_0000: nop
L_0001: ldstr "Hello World!"
L_0006: call void [mscorlib]System.Console::WriteLine(string)
```

-continued

```
L__000b: nop
L__000c: ret
```

A sample of the byte level representation is:

| | | | |
|---|---|---|---|
| [0x00000000] | 0x00 | byte | L__0000: nop |
| [0x00000001] | 0x72 | byte | L__0001: ldstr "Hello World!" |
| [0x00000002] | 0x01 | byte | |
| [0x00000003] | 0x00 | byte | |
| [0x00000004] | 0x00 | byte | |
| [0x00000005] | 0x70 | byte | |
| [0x00000006] | 0x28 | byte | L__0006: call System.Console::WriteLIne |
| [0x00000007] | 0x10 | byte | |
| [0x00000008] | 0x00 | byte | |
| [0x00000009] | 0x00 | byte | |
| [0x0000000a] | 0x0a | byte | |
| [0x0000000b] | 0x00 | byte | L__000b: nop |
| [0x0000000c] | 0x2a | byte | L__000c: ret |

Figure 4D:
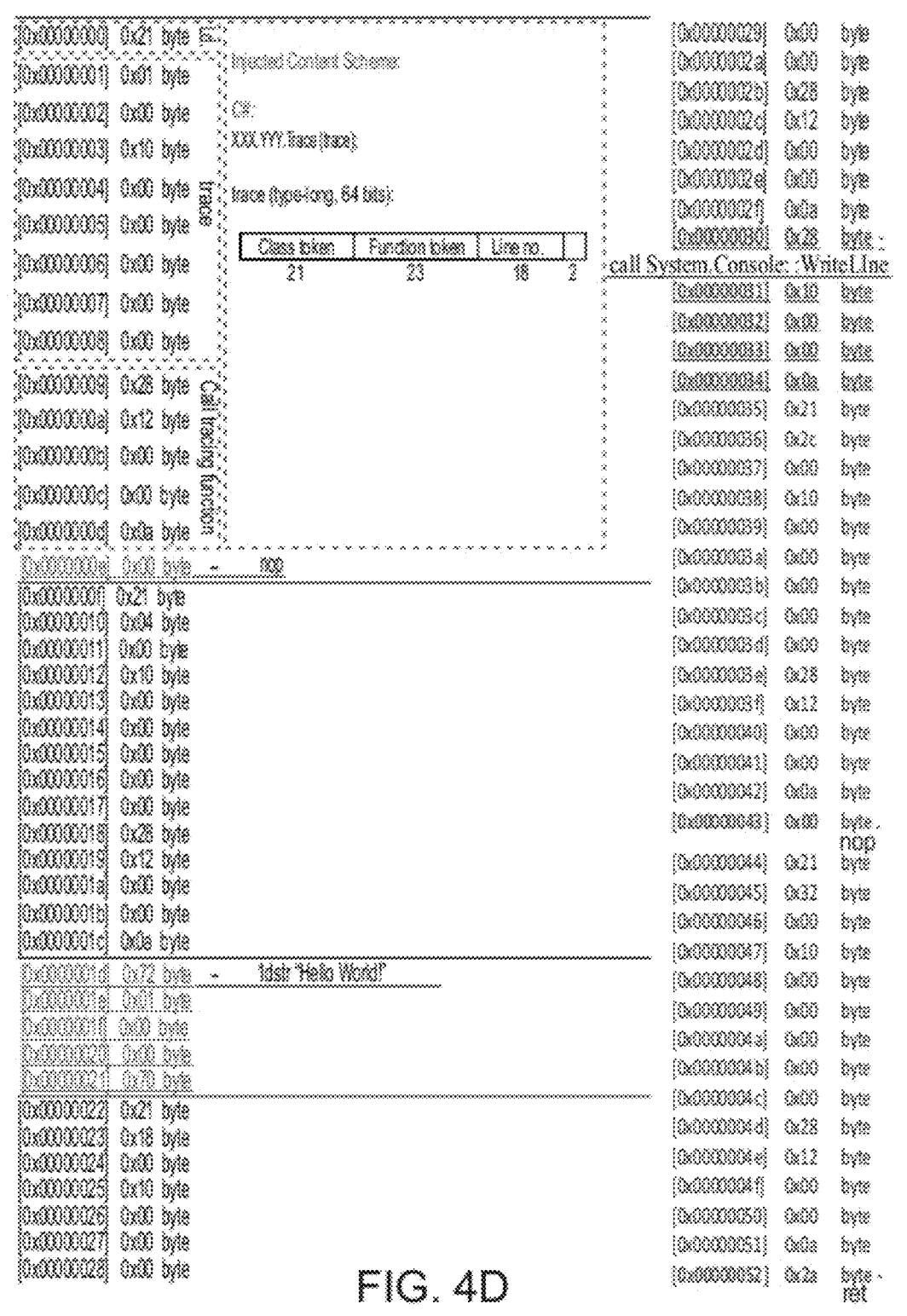

Ahead of each IL instruction, the code may be injected. In this example, the new injected code is practically a call to a tracing function, which takes a single argument that contains the necessary test information therewithin, for example as depicted in FIG. 4D. Injected segments are depicted in FIG. 4E. In FIGS. 4D-4E, the original lines are underlined.

The injection of code instructions techniques does not require any modification of the target application executable (binaries, scripts, etc) in regards of file system changes (i.e. no need to recompile and alter the original binaries of the target application), as the injection occurs during runtime.

According to some embodiments of the present invention, the routine monitor 107 includes a multi tier tracker module designed to monitor outputs of a tested application having multiple components, which are hosted in a plurality of network nodes, such as application servers.

Figure 5A:
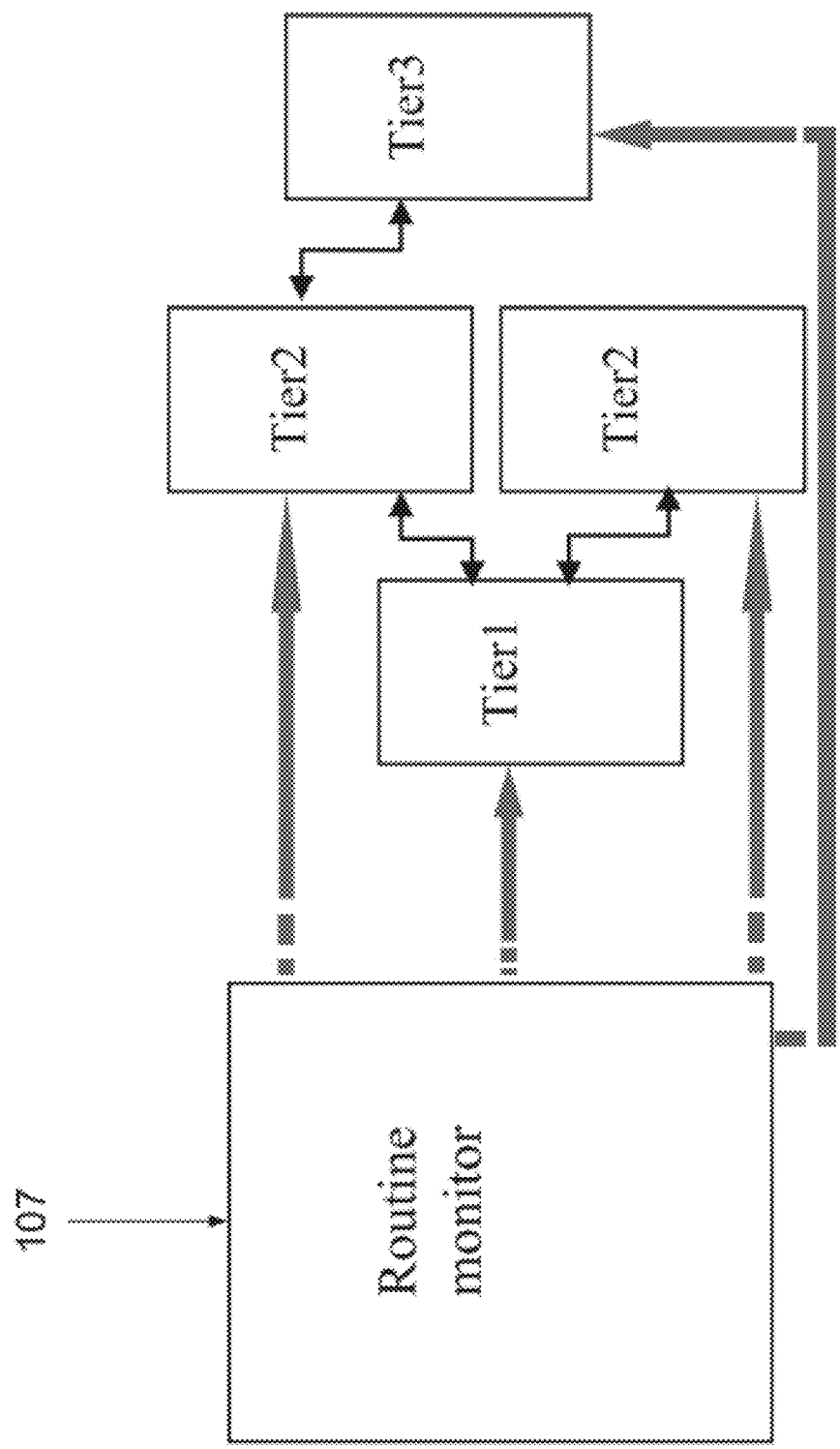
FIG. 5A is a schematic illustration of an exemplary tested application having a three tier architecture and connected to a code flow tracker, according to some embodiments of the present invention.

The multi tier tracker module is optionally used when the code flow, optionally monitored by the code flow tracker, is spread across a plurality of application components hosted by a plurality of network nodes, such as application servers, for example as the three tier architecture depicted in FIG. 5A or any other similar n-tier architecture.

In these embodiments, the first message defined in the respective testing session record 204 is for a web message, such as a request, which is sent to the first tier application component. The first tier application component invokes, in response, optionally synchronously, some operations on a second tier application component located in another web server. Optionally, the second tier application component invokes, in response, optionally synchronously, some operations on a third tier application component located in another web server, and so forth and so forth, until a final application component hosted on an n-tier network node is reached.

Figure 5B:
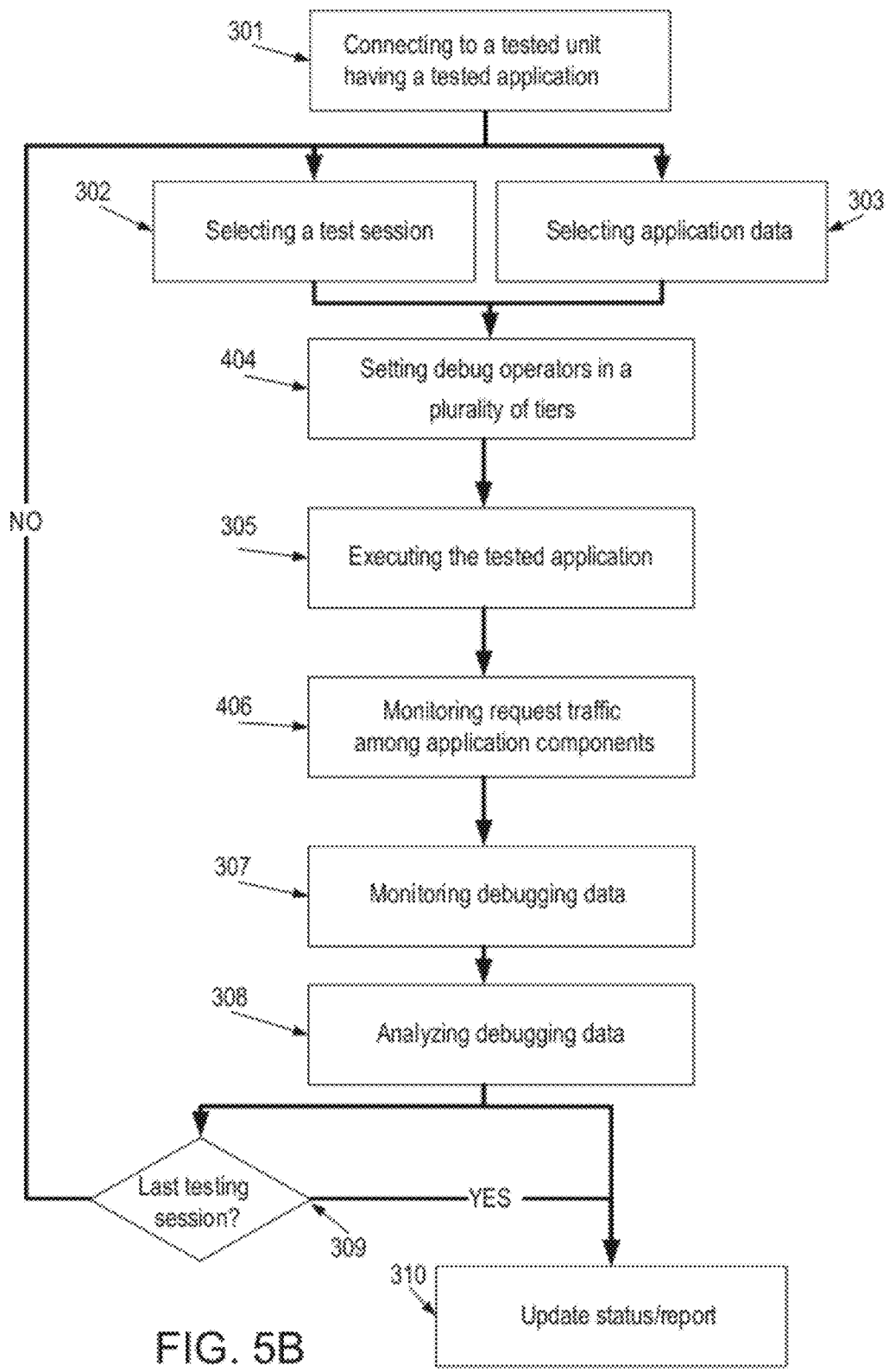
FIG. 5B is a flowchart of a method for testing security vulnerabilities in multi tier web applications, according to some embodiments of the present invention.

Reference is now made to FIG. 5B, which is a flowchart of a method for testing security vulnerabilities in multi tier web applications, according to some embodiments of the present invention.

Blocks 301-303 are as described above. At 404, the routine monitor 107 sets debug operators, such as debug hooks, breakpoints, watches, and the like, in each one of the tiers of the tested application based according to the testing instructions. The debug operators are placed in every application component in each one of the tiers. Now, as shown at 305, the tested application is executed. The debug operators allow identify system events that are relevant for the purpose of security vulnerability identification, such as DB Operation, File System access, Response Writing, Class Loading/Unloading, Memory Access, String Manipulation, Session Management, and the like. Optionally, some of the debug operators are placed to monitor data communication events, for example web service processes, communication streams, and the like.

Figure 5C:
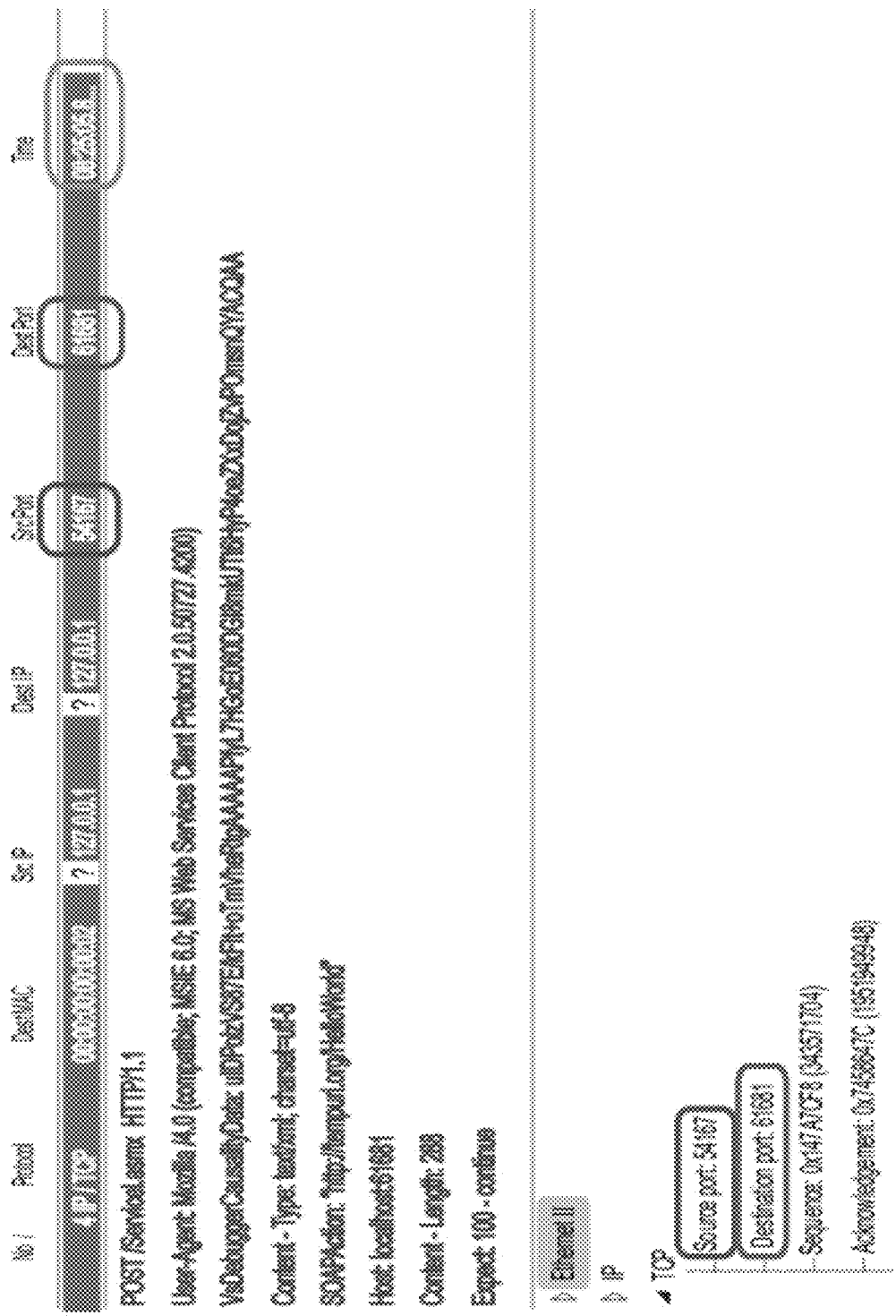
FIGS. 5C and 5D depicts samples of a web services request as identified on tier X and tier X+1 taken according to some embodiments of the present invention.
Figure 5D:
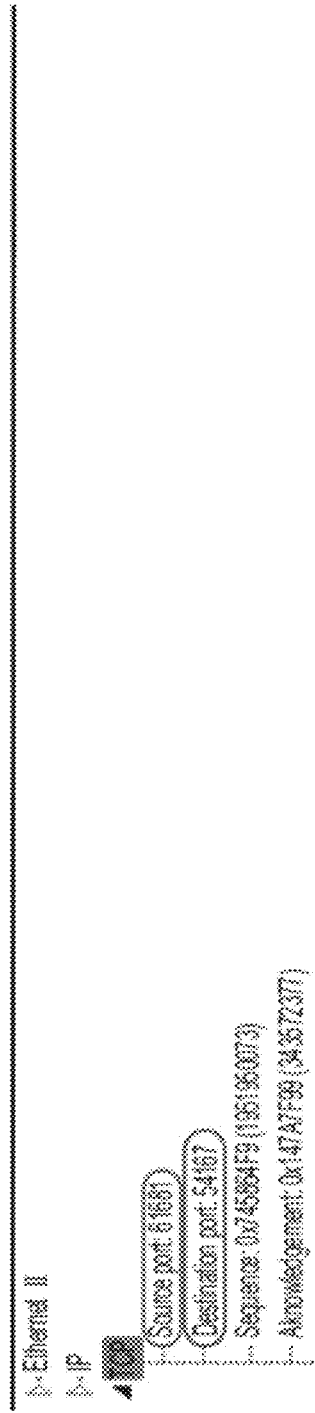

Now, the routine monitor 107 sends a request, as defined in the testing instructions, to the tested application. If the application is a web application, the request is sent to a web server which invokes the tested application and the application server it resides on. Similarly to the above, as shown at 305, the tested application receives the requests and executes it. During the execution of the tested application, the routine monitor 107 performs the automatic debugging using the set debug operators. While sending and receiving data between application components that run on the various tiers, the routine monitor 107 tracks requests and identifies the code paths among the application components in the different tiers. This is done in the following manner As shown at 406, the request traffic among the application components in different tiers is monitored. The multi tier tracker module identifies that a request for data from an application component at a new tier X+1 is sent from an application from a certain tier X. Such a request may be performed by a wide range of remote calls, including Web Services, SOAP, RMI, DCOM, and the like. When the multi tier tracker module identifies such a call, on tier X, it analyzes its destination, and it's content. Then, when the request is received by the application component on the X+1 tier, the multi tier tracker module analyzes it to identify whether this is indeed the relevant request. This verification may be performed by comparing and matching tier identification information, such as a source IP Address, a source IP Port, a timestamp, request content, a request header and the like. For example, FIGS. 5C and 5D depicts samples of a web services request as identified on tier X and tier X+1.

Optionally, if the request may lack tier identification information, the request may be intercepted at tier X. before sending it to tier X+1, and unique information may be added thereto, for example a unique request ID. In this embodiment, the unique information may be used to determine the relevancy of the request. Also, in such a scenario, the multi tier tracker module intercepts the received request at tier X+1 and removes the additional information before releasing it for execution. This guarantees that the application does not execute the modified request.

Once the request is matched, the routine monitor 107 continues the code paths analysis, similarly to the described above in relation to 307-310. The multi tier tracker module retains the tier-correlation information so that the response portion of the code flow could also be backtracked from the last tier and all the way back to the first tier.

According to some embodiment of the present invention, a report documenting the security vulnerabilities is created according to the outcome of some or all of the testing sessions.

Optionally, an exploit module or a set of instructions for creating an exploit is generated for each one of the security vulnerabilities. As commonly known, an exploit is a piece of software, a chunk of data, and/or a sequence of commands that takes advantage of the security vulnerability, which may be a bug, a glitch and the like. Optionally, the generated report includes some or all of the generated exploits, allowing demonstrating the effect of the security vulnerabilities to the operator of the tested applications. Optionally, the generation of the exploits is based on a set of instructions that is based on the security vulnerability behavior. Optionally, the report includes a vulnerable page screenshot that allows viewing the final result of the exploit and/or step-by-step instructions which provide clear instructions that allow any user of the system to reproduce the exploit directly against the tested system.

Reference is now made to an exemplary testing session in which certain security vulnerability is tested. According to some embodiments of the present invention, one or more session test records 204 include instructions that allow the scripting engine 106 to emulate injection attacks, such as a structured query language (SQL) injection, a directory traversal, a lightweight directory access protocol (LDAP) Injection, an extensible markup language (XML) path (XPath) injection, operating system (OS) commanding, a simple mail transport protocol (SMTP) injection, improper logout, username/password enumeration, no session expiration, detailed error messages, and log file injection. Optionally, the emulating is performed by creating one or more tampered testing messages which emulate an injection attack.

In such an embodiment, the scripting engine 106 injects a testing message having Meta characters that may influence the syntax of a code execution and/or the execution itself. If such an influence is detected by the testing unit 105, for example by the analyzer 203, a security vulnerability to injection attack is reported. Optionally, the response of the execution of the relevant code is monitored in runtime by the routine monitor 107 and analyzed by the analyzer 203 to probe whether the code is executed according to an expected pattern and/or in a manner that is indicative of a security vulnerability to an injection attack. Alternatively, only relevant response content is monitored in runtime by examining data generated on the probed server.

As described above, the testing may be performed interactively, according to the dataset of connected records. In such a manner, minor changes in the injected messages may be performed in each one of the iterations so as to avoid false negative detections of the scope of the security vulnerabilities.

Similarly, the messages may be used for emulating HTTP response splitting injection and/or HTTP Response carriage return line feed (CRLF) injection.

Optionally, the messages are used for emulating an injection attack that to influences an end user rather than the backend code, for example a cross site scripting (XSS). In such an embodiment, the messages are crafted by a series of uniform resource locator (URL) parameters that are sent via a URL to a dummy user. The dummy user automatically performs the attack. The identification of the XSS injection is performed in a similar manner; however the tracking of the injection is performed in a response writing component as well as correlated with the actual received response. In such a manner, a vulnerability in which a malicious data is sent to a page that stores it in the database so as to allow populating another page, which is called by another user, is emulated and detected.

As described above, the system 100 may be used for detecting SQL injections according to debugging information which is gathered in runtime. In such an embodiment, some or more testing session records define a test that allows determining whether the tested application 102 includes a combination of elements that allows executing an SQL injection in the tested unit 100. Optionally, the elements include an SQL statement in the code of the tested application and entry-point parameters concatenated into the SQL statement. Such entry-point parameters allow modifying the parameter value to a random string. In such a manner, the testing session allows identifying that the tested unit 102 allows inputting unlimited content. Such content, which is not limited to a small set of allowed values and/or formats, may allow SQL injection. Optionally, one or more testing sessions verifies whether user inputs have a syntax portion of an SQL statement. Optionally, one or more testing sessions checks whether tested values and/or parameters in the code have been used as part of the syntax of a generated SQL statement, such as a standard dynamic SQL statement or addressing a stored procedure through a dynamic SQL Injection statement.

Now, if the check is positive, an SQL injection probing is held. First, the type of the parameters in the string is checked, for example whether it is an integer or a string.

Optionally, the check is performed for parameters by inputting the following message:

Test (SQLI_P_Int) message in which a tested parameter is set to a unique identifiable integer INT having the same size as an original parameter, optionally by a representation of at least 3 bytes. If INT appears as a string value in the code flow and to reaches the SQL syntax, we proceed to another testing session according to the graph, else, no SQL Injection can be performed based on this parameter and the testing session ends.

Optionally, the check is performed for strings by inputting the following message:

Test (SQLI_P_Str) message in which a tested parameter is set to a unique identifiable alphanumeric string having the same size as the original parameter. String should include parts of an original string as well as identifiable string. If string appears as a string value in the code flow and reaches the SQL syntax, we proceed to another testing session according to the graph, else, no SQL Injection can be performed based on this parameter and the testing session ends.

Optionally, an additional test is held, for example as a separate testing session, in order to avoid false negative identification of SQL injection security vulnerability. This test is performed after the potential of SQL Injection by having parameter info embedded as part of the SQL syntax has been identified, for example as described above. Now, the actual viability of changing the SQL syntax is tested.

Optionally, the check is performed for parameters by inputting the following message:

Test (SQLI_Bas_Int) message where the parameter is set to a unique identifiable string, beginning with a part of an original integer but containing alphabetic characters having the same length limitations as described above as above. If the string appears in the code flow and reaches the SQL syntax, we proceed to another testing session according to the graph, else, no SQL Injection can be performed based on this parameter and the testing session ends. Else, the executed SQL statement is checked to determine whether the parameter in the statement appears as string, for example bounded by quotes, or as a set of integers, provided without quotes. As there may be additional characters around the injected string, such as "%" and the like, the test probes adjacent characters.

Optionally, the executed SQL statement is checked by examining the execution. If a string is probed than the query should be executed successfully. If an integer is probed the placement of alphabetic characters triggers an exception and a security vulnerability to basic Integer based SQL Injection is identified.

Optionally, if the original parameter is a string, a check is performed by inputting to the following message:

Test (SQLI_Bas_Str) message where the parameter is set to a unique identifiable string, for example as described above in relation to Test (SQLI_P_Str), but with one of the middle characters replaced with a single quote. Now, if the string appears in the code flow as before and embedded to the SQL syntax without a change, for example a single quote that remains identical and not been removed, altered to double quotes, and/or encoded, an exception occurring in the execution of the message is verified.

If no exception is verified, no SQL injection is identified and the test session is ended. Else, a security vulnerability to basic string based SQL injection is identified.

It should be noted that if a probed string may be altered however a single quote cannot be placed it is most likely that it is not possible to perform an SQL injection in an exploitable manner as it is impractical to insert alphabetic characters to perform an injection. For clarity, the detection of a security vulnerability to an SQL injection does not guarantee the exploitability of SQL injections. Optionally, the graph defines one or more exploitability tests if the testing sessions indicate on a security vulnerability to an SQL injection.

It is expected that during the life of a patent maturing from this application many relevant security vulnerability, an attack, and an injection attack will be developed and the scope of the term testing session record, a security vulnerability, an attack, and network is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for detecting at least one security vulnerability, comprising:
    providing test instructions for an application being a web application or a client server application installed at a tested unit;
    adding test code, at runtime of said application on said tested unit, to a code of said application, said code is executed on a program code execution environment of said tested unit at the runtime of said application, said test code being added according to said test instructions;
    sending via a network at least one message to said application according to said test instructions during runtime of said application;
    wherein said test code is executed on said program code execution environment of said tested unit to gather at least one reaction of said application to said at least one message during runtime of said application;
    wherein said test code is executed on said program code execution environment to forward said at least one gathered reaction from said tested unit to a testing unit which performs an analysis of said at least one reaction; and
    detecting by said testing unit a presence or an absence of at least one security vulnerability according to said analysis.

2. The method of claim 1, wherein said test code comprises at least one debug operator.

3. The method of claim 1, wherein said at least one security vulnerability is selected from a group consisting of a structured query language (SQL) injection, a directory traversal, a lightweight directory access protocol (LDAP) Injection, an extensible markup language (XML) path (XPath) injection, operating system (OS) commanding, a simple mail transport protocol (SMTP) injection, carriage return line feed (CRLF) injection, a cross site scripting (XSS), log file injection, improper logout, username/password enumeration, no session expiration, and detailer error messages.

4. The method of claim 1, wherein said test information includes data describing an influence of said at least one message on the code execution of said application at said runtime.

5. The method of claim 1, further comprising repeating said method with additional test instructions instead of said test instructions.

6. The method of claim 5, wherein said repeating is performed in each of a plurality of testing sessions; further comprising adding said at least one security vulnerability to a report in each said testing session.

7. The method of claim 5, wherein each said testing session being selected according an outcome of a previous testing session.

8. The method of claim 1, further comprising establishing a connection to with an application and using said connection for identifying said at least one reaction, said providing being performed according to said identifying.

9. The method of claim 1, further comprising providing a model defining a plurality of connections among a plurality of testing session records outlining at least a portion of said test instructions; wherein at least said sending and said monitoring are repetitively performed in a plurality of testing sessions selected according to said model and defined according to a group of said plurality of testing session records.

10. The method of claim 9, wherein at least one member of said group is selected according to an outcome of at least one of said plurality of testing sessions.

11. The method of claim 1, further comprising monitoring behavioral changes of an original code of said application at said runtime period and performing said detecting according to said changes.

12. The method of claim 1, wherein said detecting comprises detecting a code segment posing said security vulnerability in the code of said application;
further comprising presenting said code segment to a user.

13. The method of claim 1, further comprising generating an exploit module to said security vulnerability and providing said exploit module to a user.

14. The method of claim 13, further comprising generating a report including said exploit module so as to allow the demonstrating of said security vulnerability.

15. The method of claim 14, wherein said report includes at least one of a vulnerable page screenshot that allows viewing the final result of said security vulnerability and a set of step-by-step instructions that define how to reproduce said security vulnerability.

16. The method of claim 13, wherein said generating is performed according to a set of instructions that is based on a behavior of said security vulnerability.

17. The method of claim 1, wherein said detecting comprises identifying a functionality of a validation/sanitation filter.

18. The method of claim 17, wherein said identifying is performed by identifying an attack not filtered by said validation/sanitation filter.

19. The method of claim 1, wherein said providing comprises selecting data application record describing an interface data pertaining to said application from a plurality of data application records, tracking whether a certain string being modified at said runtime, and generating said at least one message according to said data application.

20. The method of claim 1, wherein said monitoring comprises tracking whether a certain string being modified at said runtime, said string is a member of a group consisting of a string provided by said at least one message, at least a portion of a string that function as an input of an executed code of said application, and an output of said application.

21. The method of claim 1, wherein said monitoring comprises tracking a runtime exception at said runtime, said detecting being performed according to said runtime exception.

22. The method of claim 1, wherein said application having a plurality of application components in a plurality of network nodes, said adding comprises adding at least one debug operator to each said application component, said monitoring comprises monitoring message traffic between said plurality of application components.

23. The method of claim 1, wherein said test code comprises at least one profiling object.

24. A system for detecting at least one security vulnerability at runtime, comprising:
a repository storing test instructions;
a network interface for sending at least one message to an application according to said test instructions at runtime thereof, said application being a web application or a client server application installed on a tested unit;
a code interface for adding a test code on said tested unit to a code of said application which is executed on a program code execution environment of said tested unit at runtime of said application, said test code being added according to said test instructions, wherein said test code is executed on said program code execution environment of said tested unit to gather at least one reaction of said application to said at least one message during runtime of application; and
a circuit which runs instructions for detecting at least one security vulnerability according to an analysis of said at least one gathered reaction.

25. The system of claim 24, wherein said repository stores a plurality of testing session records defining at least a portion of said test instructions, said network interface being configured for sending a plurality of messages in a plurality of testing sessions, each said message being generated according to a different member of a group of said plurality of testing session records.

26. The system of claim 24, wherein said code interface comprises a code flow tracker that facilitates a code coverage aggregation, said testing unit detects said at least one security vulnerability according to an analysis if said code coverage aggregation.

27. The system of claim 24, wherein said code interface comprises a code flow tracker that compares code flow outlines of a multi parameter message with different parameter combinations, said testing unit detects said at least one security vulnerability by an analysis of an executed code generated in response to said multi parameter message.

28. The system of claim 25, further comprising a model defining a plurality of connection among said plurality of testing session records, said group being gradually generated at said runtime according to said plurality of connection.

29. The system of claim 24, wherein said repository stores a plurality of testing session records, further comprising an analyzer configured for managing a testing process by dynamically selecting at least one of said plurality of testing sessions according to said test information, said at least one message being defined according to said at least one testing session.

30. A method for detecting at least one security vulnerability, comprising:
a) providing a plurality of testing session records each defining a test session for a security vulnerability assessment and a model defining a plurality of connections among said testing session records;
b) testing an application according to one of said plurality of testing session records, said application being a web application or a client server application installed at a tested unit;
c) performing an analysis of a reaction of said application to said test session during the execution of said application;
d) selecting an additional of said plurality of testing session records according to said model in the light of said analysis; and
e) repeating said b) and c) where said testing being held according to said additional testing session;
wherein said testing comprises injecting test code to a code of said application on said tested unit, which is executed on a program code execution environment at runtime of said application to gather at least one reaction of said during runtime of said application.

31. The method of claim 30, wherein said analysis is of performed according to data aggregated during a previous testing session where said testing is held according to a previous testing session.

32. A method for detecting at least one security vulnerability, comprising:
a) providing test instructions for a multitier application having a plurality of application components in a plurality of network nodes, each said application component being of a different tier;
b) adding, at runtime of said application, at least one debug operator to a program code execution environment wherein a code of each said application component is executed according to said test instructions;
c) invoking a data communication event between said application component components at runtime of said application;
d) identifying a first message sent from a first tier application component to a second tier application component and a second message received by said second tier application component;
e) identifying a code path among said plurality of application components by a comparison between first identification information of said first message and second identification information of said second message; and,
f) detecting a presence or an absence of at least one security vulnerability according to said code path.

33. The method of claim 32, further comprising repeating d) and e) with another pair of said plurality of application components.

34. The method of claim 32, further comprising adding said first identification information to said first message.

35. A method for detecting at least one security vulnerability, comprising:
providing test instructions for an application being a web application or a client server application installed at a tested unit;
injecting at least one instruction to a code of said application which is executed on a program code execution environment according to said test instructions at runtime thereof;
executing said test code on said program code execution environment to gather at least one reaction of said at least one instruction during runtime of said application;
performing an analysis of said at least one gathered reaction; and
detecting a presence or an absence of at least one security vulnerability according to said analysis.

36. The method of claim 35, wherein said monitoring is performed using a profiling mechanism.

* * * * *